United States Patent
Stapelfeldt et al.

(10) Patent No.: US 9,622,709 B2
(45) Date of Patent: Apr. 18, 2017

(54) MONITORING SEVERITY AND DURATION OF ABERRANT PHYSIOLOGICAL PARAMETERS DURING A PROCEDURE

(71) Applicant: THE CLEVELAND CLINIC FOUNDATION, Cleveland, OH (US)

(72) Inventors: Wolf H. Stapelfeldt, Jacksonville, FL (US); Marc R. Reynolds, Shaker Hts., OH (US); Bhaswati Ghosh, Shaker Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 539 days.

(21) Appl. No.: 14/051,902

(22) Filed: Oct. 11, 2013

(65) Prior Publication Data
US 2014/0107504 A1 Apr. 17, 2014

Related U.S. Application Data

(60) Provisional application No. 61/712,875, filed on Oct. 12, 2012.

(51) Int. Cl.
*A61B 5/021* (2006.01)
*A61B 5/00* (2006.01)

(52) U.S. Cl.
CPC .......... *A61B 5/7275* (2013.01); *A61B 5/0022* (2013.01); *A61B 5/021* (2013.01);
(Continued)

(58) Field of Classification Search
CPC ..... A61B 5/0022; A61B 5/021; A61B 5/4821; A61B 5/4848; A61B 5/7275; A61B 5/746; A61B 5/7475
See application file for complete search history.

(56) References Cited

U.S. PATENT DOCUMENTS

2009/0124867 A1 5/2009 Hirsh
2011/0257535 A1* 10/2011 Michelson ......... A61B 5/02405
600/484

(Continued)

FOREIGN PATENT DOCUMENTS

EP 2407218 A2 1/2012

OTHER PUBLICATIONS

Bijker et al, Intraoperative Hypotension and 1-Year Mortality after Noncardiac Surgery, 2009, Anesthesiology, 111: 1217-26.*
(Continued)

*Primary Examiner* — Jacqueline Cheng
*Assistant Examiner* — Angeline Premraj
(74) *Attorney, Agent, or Firm* — Tarolli, Sundheim, Covell & Tummino LLP

(57) ABSTRACT

Systems and methods are provided for monitoring a patient during a procedure. A physiological parameter of a patient is monitored during a procedure at an associated sensor. Respective cumulative times are measured for which the monitored physiological parameter of the patient meets each of a plurality of threshold values during the procedure. A risk metric is calculated for the patient, representing an effect of monitored physiological parameter on a patient outcome related to the procedure from the measured cumulative times for which the monitored physiological parameter of the patient met each of the plurality of threshold values.

16 Claims, 10 Drawing Sheets

(52) U.S. Cl.
CPC .......... *A61B 5/4821* (2013.01); *A61B 5/4848* (2013.01); *A61B 5/746* (2013.01); *A61B 5/7475* (2013.01)

(56) References Cited

U.S. PATENT DOCUMENTS

| | | | |
|---|---|---|---|
| 2012/0053433 A1 | 3/2012 | Chamoun | |
| 2012/0109243 A1* | 5/2012 | Hettrick | G06F 19/3418 607/17 |
| 2012/0196293 A1* | 8/2012 | Juo | C12Q 1/6883 435/6.12 |
| 2012/0277546 A1* | 11/2012 | Soykan | A61B 5/0205 600/301 |

OTHER PUBLICATIONS

PCT International Search Report and Written Opinion, mailed Jan. 24, 2014, pp. 1-14.

\* cited by examiner

MONITORING SEVERITY AND DURATION OF ABERRANT PHYSIOLOGICAL PARAMETERS DURING A PROCEDURE

RELATED APPLICATION

The present application claims priority to U.S. Provisional Patent Application Ser. No. 61/712,875 filed Oct. 12, 2012 entitled DETECTION OF HYPOTENSIVE EXPOSURE DURING ANESTHESIA, the entire contents of which being incorporated herein by reference in its entirety for all purposes.

FIELD OF THE INVENTION

The present invention relates to systems and methods for monitoring patients under anesthesia or procedural sedation and, in particular, is directed to systems and methods for monitoring severity and duration of aberrant physiological parameters during a procedure.

BACKGROUND OF THE INVENTION

Anesthesia has traditionally meant the condition of having sensation, including the feeling of pain, blocked or temporarily taken away. It is a pharmacologically induced and reversible state of amnesia, analgesia, loss of responsiveness, loss of skeletal muscle reflexes or decreased stress response, or all simultaneously. These effects can be obtained from a single drug which alone provides the correct combination of effects, or occasionally a combination of drugs, such as hypnotics, sedatives, paralytics and analgesics, to achieve very specific combinations of results. This allows patients to undergo surgery and other procedures without the distress and pain they would otherwise experience. An alternative definition is a "reversible lack of awareness," including a total lack of awareness (e.g. a general anesthetic) or a lack of awareness of a part of the body such as a spinal anesthetic.

SUMMARY OF THE INVENTION

In accordance with an aspect of the present invention, a method is provided for monitoring a patient during a procedure. A physiological parameter of a patient is monitored during a procedure at an associated sensor. Respective cumulative times are measured for which the monitored physiological parameter of the patient meets each of a plurality of threshold values during the procedure. A risk metric is calculated for the patient, representing an effect of monitored physiological parameter on a patient outcome related to the procedure from the measured cumulative times for which the monitored physiological parameter of the patient met each of the plurality of threshold values.

In accordance with another aspect of the present invention, a non-transitory computer readable medium stores machine executable instructions executable at an associated processor to predict patient outcomes related to a procedure. A feature extractor is configured to provide a plurality of features from a physiological parameter measured for a patient during the procedure. The plurality of features includes at least cumulative time periods for which a value of a parameter meets various thresholds of the monitored parameter. A predictive model is configured to calculate a risk metric, representing an effect of monitored physiological parameter on a patient outcome related to the procedure from the measured cumulative times for which the monitored physiological parameter of the patient met each of the plurality of threshold values. A user interface is configured to provide the calculated risk metric to a user in a human comprehensible form.

In accordance with yet another an aspect of the present invention, a system for predicting patient outcomes relating to a procedure is implemented on at least one dedicated hardware device. The system includes a sensor configured to detect physiological parameters of a patient during the procedure and a user interface. A processing assembly is configured to compare the detected physiological parameter to a plurality of defined ranges, record cumulative times for which the measured physiological parameter deviate from each of the defined ranges, and notify an operator each time the cumulative time that measured physiological parameters exceeds a maximum time associated with a given defined range, portending a certain percent increase in risk of adverse outcome.

In accordance with still another aspect of the invention, a method is provided for detecting hypotensive exposure during anesthesia. A blood pressure of a patient is monitored during a procedure at a blood pressure sensor. Respective cumulative times for which the blood pressure of the patient was below each of a plurality of threshold values during the procedure are measured. A user is alerted when any one of the cumulative times exceeds a predetermined exposure limit for its associated threshold value, portending a certain percent increase in risk of adverse outcome. Furthermore, a final risk score can be provided at the end of a procedure based on the total number of exposure limits that were exceeded over the course of the procedure.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
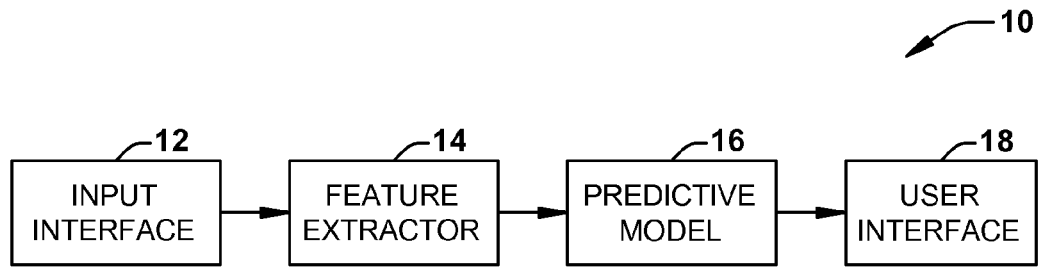
FIG. 1 illustrates a system for predicting the likelihood of adverse outcomes related to a procedure in accordance with an aspect of the present invention.

As part of anesthesia, it is common for patients to experience a decrease in blood pressure. Severe enough blood pressure decreases during anesthesia have the potential for adversely affecting postoperative patient outcome. Other, similar conditions, such as hypoxia, can also result in adverse outcomes. Accordingly, the use of anesthesia is associated with considerable risk not only the procedure but also with regard to post-procedure complications, such as morbidity and death within thirty days. The present invention addresses the need to be able to detect deviations in physiological parameters having sufficient severity and duration to portend adverse patient outcome in the days and weeks following a procedure. FIG. 1 illustrates a system 10 for predicting the likelihood of adverse outcomes related to a procedure in accordance with an aspect of the present invention. In one implementation, the adverse outcome can be one of in-hospital morbidity or mortality, morbidity or mortality within a thirty-day period after a procedure, an increase in length of hospital stay, or readmission to a hospital within a thirty-day period after a procedure. Specifically, the illustrated system 10 utilizes parameters derived from biometric measurements taken during the procedure, for example, while the patient is under general anesthesia. It will be appreciated that the illustrated system 10 can be implemented as dedicated hardware, for example, implemented within a sensor assembly for sensing the physiological parameter, software instructions stored on one or more non-transitory computer readable media operatively connected to an associated processor, or a combination of hardware and software. Dedicated hardware devices for implementing the system can include, for example, application specific integrated circuits (ASICs), programmable logic devices (PLDs), and field-programmable gate arrays (FPGAs).

An input interface 12 is configured to receive a plurality of parameters derived from physiological measurements taken during the procedure. In one implementation, the input interface 12 can comprise machine readable instructions for providing an input screen to a user to allow the user to enter the plurality of parameters via an appropriate input device (e.g., keyboard, mouse, microphone, camera, touch screen, etc.). In an alternative implementation, the input interface 12 is configured to interact with a medical database, blood pressure measurement device, or other automated data source to extract the plurality of parameters from medical records, an anesthesia record, or native blood pressure recordings associated with a given procedure.

These parameters are provided to a feature extractor 14. In accordance with an aspect of the present invention, a plurality of features used in predicting the likelihood of an adverse patient outcome include cumulative time periods for which a value of a parameter meets various thresholds of the monitored parameter, that, the accumulated sum of the durations of each incident in which the threshold is met. For example, in one implementation, the cumulative time for which a patient's mean arterial blood pressure falls below each threshold value is measured. The feature extractor 14 therefore analyzes the provided parameters and determines for each parameter threshold a cumulative amount of time for which the patient had value meeting the threshold. It will be appreciated that this can be repeated for multiple thresholds, with a separate cumulative time spent below the threshold value determined for each threshold value.

The parameters derived for the plurality of features are provided to a predictive model 16, which is configured to calculate a risk metric representing a likelihood of an adverse patient outcome from the plurality of features as a linear or non-linear combination of mathematical functions of the plurality of features. In one implementation, the mathematical functions are step functions, such that the function is a first value when the cumulative time for a given threshold value is below a value associated with the step function and a second value when the cumulative time is above the value. Accordingly, in one example, the risk metric can comprise a number of mean arterial blood pressure thresholds that were met for cumulative times exceeding certain predetermined values, such as one minute or a certain number of minutes. In the illustrated implementation, each of the plurality of features has an associated weight, and the predictive model 16 provides a weighted combination of the plurality of features themselves or some mathematical function of each feature. It will be appreciated, however, that the predictive model 16 can utilize any appropriate classification or regression model, such as an artificial neural network, a support vector machine, a statistical classifier, or a similar model, to calculate the risk metric, and that in some implementations, the calculated risk metric can be categorical, such that it represents one of a plurality of risk classes. A user interface 18 is configured to provide the calculated risk matric to a user in a human comprehensible form. Specifically, the user interface 18 interacts with a display, printer, speaker, or other appropriate output device to provide the calculated likelihood of an adverse patient outcome to a user.

Figure 2:
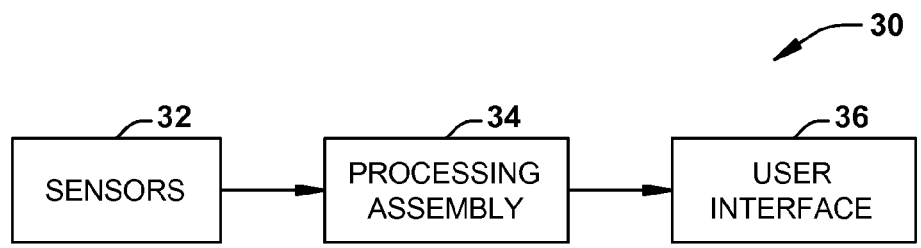
FIG. 2 depicts one example of a patient monitoring system in accordance with an aspect of the present invention.

FIG. 2 depicts one example of a patient monitoring system 30 in accordance with an aspect of the present invention. The system 30 includes a plurality of sensors 32, depicted here collectively for simplicity, to measure physiological parameters of a patient during a procedure and, in the illustrated implementation, under anesthesia. In one example, the plurality of sensors 32 can include sensors for monitoring one or more of electrocardiography (ECG) data, heart rate, blood pressure, inspired and expired gases, oxygen saturation of the blood (pulse oximetry), temperature, urine output, central venous pressure, pulmonary artery pressure and pulmonary artery occlusion pressure, cardiac output, cerebral activity, and neuromuscular function. In the illustrated implementation, one of the monitored parameters includes a mean arterial blood pressure, and monitoring of the mean arterial blood pressure is used as an example for the sake of explanation. It will be appreciated, however, that the system 30 can monitor other parameters or multiple physiological parameters in a similar manner.

Data from the plurality of sensors 32 is provided to a processing assembly 34 that monitors and records the received data. In one implementation, the processing assembly 34 comprises a hardware processor and software instructions stored on one or more non-transitory computer readable media, although it will be appreciated that alternative implementations, such as dedicated hardware devices, are possible. The processing assembly 34 includes, for selected parameters, respective defined ranges for the parameters, with the processing assembly 34 notifying a user of any deviations of the measured parameters from the defined ranges that exceed associated maximum cumulative times at an associated user interface 36. In practice, the ranges can be open ended, such that the range merely defines an upper or lower boundary for its associated parameter. It will be appreciated that the defined ranges can be specific to the patient, for example, to reflect other biometric parameters of the patient, such as age, existing medical conditions, height, and weight. The user interface 36 can include any appropriate means for providing a visible or audible signal to the user, such as a display, an LED or other light-emitting indicator, and a speaker, as well as an input means, such as a touch screen, mouse, keyboard, or microphone, for receiving instructions from the user.

In accordance with an aspect of the present invention, the plurality of defined ranges include a plurality of thresholds for the minute-to-minute mean arterial blood pressure, such that a user is alerted whenever the patient's cumulative time spent at a mean arterial blood pressure below a given one of the threshold values exceeds a corresponding exposure limit for the threshold. In one implementation, a first threshold is defined at seventy-five mm Hg, and each successive threshold is defined at a value one mm Hg less than that of the preceding threshold up to a final threshold of forty-five mm Hg. As each threshold is met, the processing assembly 34 can monitor a cumulative time for which the mean arterial blood pressure has been below the threshold. These cumulative times can be compared to predetermined exposure time limits, which can be generic or customized to the patient and/or by the user, and alert the user to the increased risk of post-procedure morbidity or mortality as the cumulative time approaches or exceeds these limits. The inventors have determined that the predicted patient risk for increased 30-day mortality can be related to the number of cumulative time limits exceeded for time spent below the various blood pressure threshold values. It will be appreciated that the extracted features can also include other relevant parameters, such as the patient's age, the Charlson Comorbidity Index, and an amount of blood lost by the patient during the procedure. It will further be appreciated that exposure limits portending equivalent risk may be different for patients with different conditions such as a history of hypertension.

In addition to alerting the user when a threshold is exceeded or an increase in risk that occurs during a procedure, with the goal of potentially minimize any further progression of postoperative risk attributable to the aberrant physiologic parameter, the system 30 can also be used to identify and stratify patients after the procedure for more intensive postprocedure follow-up care due to risk portended by the severity and duration of aberrant levels of physiological parameters that were experienced during the procedure. Such patients could be targeted for additional care and monitoring to minimize whatever effects the aberrant parameters may have on the patient outcome. For example, in the case of hypotension, additional cardiac monitoring can be conducted both within a hospital and after release of the patient to mitigate the increased risk incurred due to the patient's hypotensive state experienced during the procedure, such as that reflected in the total number of hypotensive exposure limits that were exceeded during the procedure.

Figure 3:
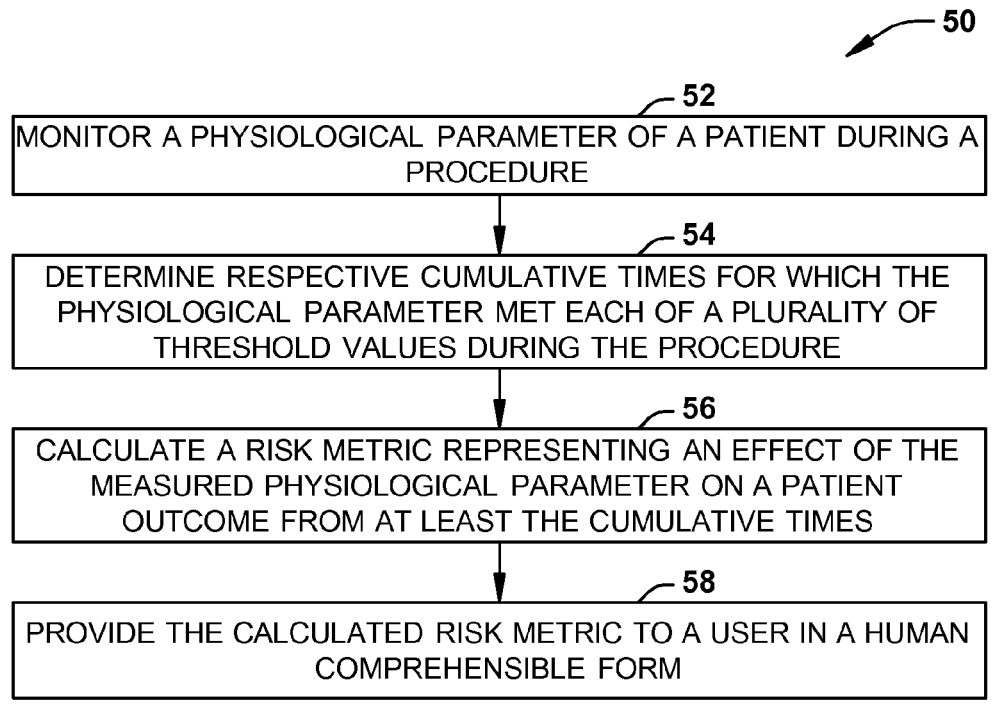
FIG. 3 illustrates a method for predicting a patient outcome from a physiological parameter recorded during the procedure in accordance with an aspect of the present invention.
Figure 4:
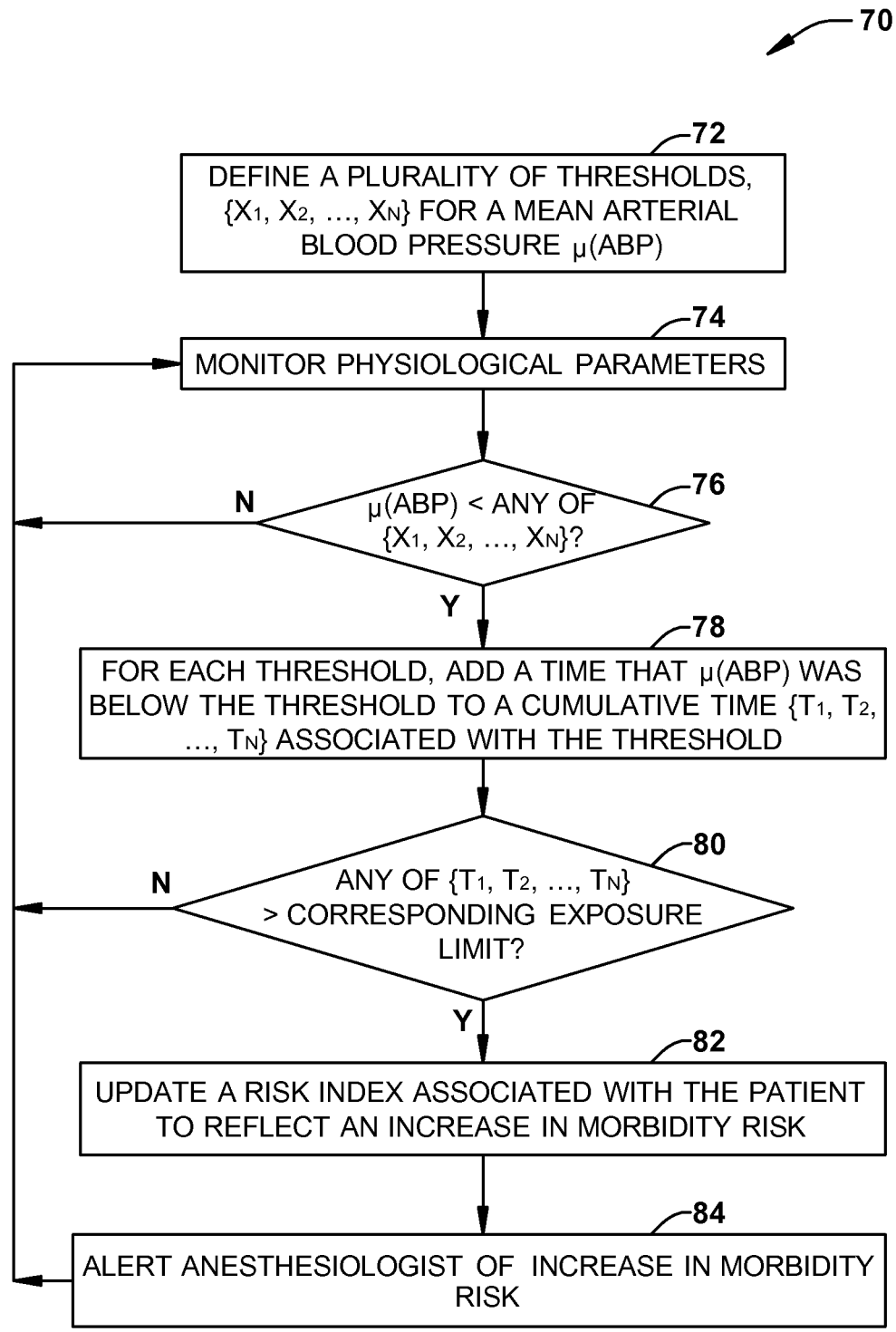
FIG. 4 illustrates an example method for monitoring a mean arterial blood pressure during a procedure utilizing anesthesia in accordance with an aspect of the present invention.

In view of the foregoing structural and functional features described above, a methodology in accordance with various aspects of the present invention will be better appreciated with reference to FIGS. 3 and 4. While, for purposes of simplicity of explanation, the methodologies of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described.

FIG. 3 illustrates a method 50 for predicting a patient outcome from a physiological parameter recorded during the procedure in accordance with an aspect of the present invention. At 52, a physiological parameter of a patient is monitored during a procedure at an associated sensor. At 54, respective cumulative times are measured for which the monitored physiological parameter of the patient meets each of a plurality of threshold values during the procedure These cumulative times, along with other biometric and biographical parameters of the patient can be used as a plurality of features for a predictive model. At 56, a risk metric is calculated for the patient, representing an effect of monitored physiological parameter on a patient outcome related to the procedure from the measured cumulative times for which the monitored physiological parameter of the patient met each of the plurality of threshold values. At 58, the calculated risk metric is provided to a user in a human comprehensible form.

FIG. 4 illustrates an example method 70 for monitoring a mean arterial blood pressure during a procedure utilizing anesthesia in accordance with an aspect of the present invention. At 72, a plurality of mean arterial blood pressure thresholds are defined for the patient. For ease of reference, the mean arterial blood pressure is represented as (ABP) in FIG. 4 and an $i^{th}$ mean arterial blood pressure threshold of a sequence of thresholds is denoted in FIG. 4 as $X_i$. The threshold values as well as the maximum cumulative times permissible exceeding these threshold values can be defined via any appropriate means, including individually for each patient based on a patient history as, for example, extracted from an electronic health records (EHR) system; applicable to certain patient populations (such as adult patients undergoing non-cardiac surgery); selected as a list of standard threshold values; derived from a determined minimum or maximum threshold for the patient and a standardized inter-threshold interval; or provided by a user at an associated input device.

At 74, various physiological parameters of the patient are monitored, including the minute-to-minute mean arterial blood pressure. It will be appreciated that this monitoring will generally be performed continuously or intermittently (such as within a certain number of minutes, in accordance with applicable monitoring standards) throughout the method 70. At 76, it is determined if the mean arterial blood pressure has fallen below any of the threshold values during a given interval. If not (N), the method returns to 74 where the biometric parameters continue to be monitored. If the mean arterial blood pressure has fallen below one or more of the threshold values (Y), the method advances to 78, where a cumulative amount of time associated with each threshold is updated to reflect the amount of time that the patient's mean arterial blood pressure was below that threshold during a previous measurement interval.

At 80, the cumulative time for each threshold is compared to a corresponding exposure limit. For example, the various exposure limits can be determined as a maximum amount of time that a patient can remain below the associated threshold without experiencing a certain increase in the risk of post-procedure morbidity or mortality. The exposure limits can vary for the plurality of thresholds, and can be standardized, determined individually for each patient according to an associated patient history, for example, by querying an EHR database for certain diagnoses or by entering such information via an appropriate input device. In one implementation, the exposure limits can be selected to be the time periods associated with certain progressive increases in post-procedure morbidity or mortality that are portended by each additional exposure limit exceeded so as to provide an anesthesiologist an opportunity to react to the hypotensive state before it represents a risk of certain magnitude to the patient. In one example, dealing with blood pressure thresholds for monitoring hypotension, the exposure limits can be selected according to a patient's absence or presence of a history of hypertension. An example of a standard set of applicable blood pressure threshold values as well as corresponding exposure time limits for time accumulated below these thresholds (in minutes) portending various levels of risk for 30-day mortality in normal patients is provided as Table 1. A corresponding table for patients with a history of hypertension is provided as Table 2.

TABLE 1

| normotensive | 5% | 10% | 15% | 20% | 25% | 30% | 35% | 40% | 45% | 50% |
|---|---|---|---|---|---|---|---|---|---|---|
| 75 | 26.6 | 51.9 | 76.1 | 99.3 | 121.5 | 142.8 | 163.4 | 183.2 | 202.8 | 220.8 |
| 74 | 22.9 | 44.7 | 65.55 | 86.5 | 104.6 | 123.0 | 140.7 | 157.8 | 174.2 | 190.1 |
| 73 | 19.9 | 38.8 | 56.9 | 74.3 | 90.9 | 106.9 | 122.3 | 137.1 | 151.4 | 165.2 |
| 72 | 17.5 | 34.1 | 50.1 | 65.3 | 79.9 | 94.0 | 107.5 | 120.5 | 133.1 | 145.2 |
| 71 | 15.4 | 30.1 | 44.2 | 57.6 | 70.5 | 82.9 | 94.8 | 106.3 | 117.4 | 128.1 |
| 70 | 13.6 | 26.5 | 38.8 | 50.7 | 62.0 | 72.9 | 83.4 | 93.5 | 108.2 | 112.7 |
| 69 | 11.9 | 23.3 | 34.2 | 44.6 | 54.5 | 64.1 | 73.3 | 82.2 | 90.8 | 99.1 |
| 68 | 10.5 | 20.6 | 30.2 | 39.4 | 48.2 | 56.7 | 64.9 | 72.8 | 80.3 | 87.7 |
| 67 | 9.3 | 18.2 | 26.7 | 34.8 | 42.6 | 50.1 | 57.3 | 64.2 | 70.9 | 77.4 |
| 66 | 8.3 | 16.2 | 23.8 | 31.1 | 38.0 | 44.7 | 51.2 | 57.4 | 63.8 | 69.1 |
| 65 | 7.3 | 14.3 | 21.0 | 27.4 | 38.6 | 39.5 | 45.1 | 50.6 | 55.9 | 61.0 |
| 64 | 6.7 | 19.0 | 19.1 | 24.9 | 30.4 | 35.8 | 40.9 | 45.9 | 50.7 | 55.3 |
| 63 | 6.0 | 11.7 | 17.1 | 22.3 | 27.3 | 32.1 | 36.7 | 41.1 | 45.4 | 49.6 |
| 62 | 5.3 | 10.4 | 15.2 | 19.9 | 24.3 | 28.6 | 32.7 | 36.6 | 40.5 | 44.2 |
| 61 | 4.2 | 9.2 | 19.5 | 17.6 | 21.6 | 25.4 | 29.0 | 82.6 | 36.0 | 39.2 |
| 60 | 4.2 | 8.3 | 12.2 | 15.9 | 19.4 | 22.8 | 26.1 | 29.3 | 32.3 | 35.8 |
| 59 | 3.7 | 7.2 | 10.6 | 13.8 | 16.9 | 19.9 | 22.8 | 22.5 | 28.2 | 30.8 |
| 58 | 3.2 | 6.3 | 9.3 | 12.1 | 14.9 | 17.5 | 20.0 | 22.4 | 24.7 | 27.0 |
| 57 | 2.8 | 5.5 | 8.1 | 10.6 | 13.0 | 15.3 | 17.4 | 19.6 | 21.6 | 23.6 |
| 56 | 2.4 | 4.7 | 6.9 | 9.0 | 11.0 | 13.0 | 14.8 | 16.6 | 18.4 | 20.0 |
| 55 | 2.0 | 4.0 | 5.9 | 7.7 | 9.4 | 11.0 | 12.6 | 14.1 | 15.6 | 17.0 |
| 54 | 1.7 | 3.4 | 5.0 | 6.5 | 8.0 | 9.4 | 10.7 | 12.0 | 13.3 | 14.5 |
| 53 | 1.5 | 2.9 | 4.3 | 5.6 | 6.9 | 8.1 | 9.2 | 10.3 | 11.4 | 12.5 |
| 52 | 1.3 | 2.5 | 3.7 | 4.8 | 5.9 | 7.0 | 8.0 | 8.9 | 9.9 | 10.8 |
| 51 | 1.1 | 2.1 | 3.1 | 4.1 | 5.0 | 5.9 | 6.7 | 7.5 | 8.3 | 9.1 |
| 50 | 0.9 | 1.8 | 2.6 | 3.4 | 4.2 | 5.0 | 5.7 | 6.4 | 7.0 | 7.7 |
| 49 | 0.8 | 1.6 | 2.3 | 3.0 | 3.6 | 4.3 | 4.9 | 5.5 | 6.0 | 6.6 |
| 48 | 0.7 | 1.3 | 2.0 | 2.6 | 3.1 | 3.7 | 4.2 | 4.7 | 5.2 | 5.7 |
| 47 | 0.6 | 1.2 | 1.7 | 2.2 | 2.7 | 3.2 | 3.7 | 4.1 | 4.6 | 5.0 |
| 46 | 0.5 | 1.0 | 1.5 | 2.0 | 2.4 | 2.8 | 8.3 | 3.7 | 4.0 | 4.4 |
| 45 | 0.5 | 0.9 | 1.3 | 1.7 | 2.1 | 2.5 | 2.9 | 3.2 | 3.6 | 8.9 |

TABLE 2

| hypertensive | 5% | 10% | 15% | 20% | 25% | 30% | 35% | 40% | 45% | 50% |
|---|---|---|---|---|---|---|---|---|---|---|
| 75 | 16.9 | 33.1 | 48.5 | 63.3 | 77.5 | 91.1 | 104.2 | 116.8 | 129.0 | 140.8 |
| 74 | 15.0 | 29.4 | 43.0 | 56.1 | 68.7 | 80.8 | 92.4 | 103.6 | 114.4 | 124.9 |
| 73 | 13.5 | 26.4 | 38.8 | 50.6 | 61.9 | 72.8 | 83.2 | 98.3 | 103.0 | 112.4 |
| 72 | 12.3 | 24.0 | 35.2 | 45.9 | 56.2 | 66.1 | 75.6 | 84.7 | 93.6 | 102.1 |
| 71 | 11.1 | 21.7 | 31.8 | 41.4 | 50.7 | 59.6 | 68.2 | 76.5 | 84.5 | 92.2 |
| 70 | 10.0 | 19.6 | 28.8 | 37.5 | 45.9 | 54.0 | 61.8 | 69.3 | 76.5 | 83.5 |
| 69 | 9.1 | 17.7 | 26.0 | 33.9 | 41.4 | 48.7 | 55.7 | 62.5 | 69.0 | 75.3 |
| 68 | 8.2 | 16.1 | 28.6 | 30.7 | 37.6 | 44.2 | 50.6 | 56.7 | 62.6 | 68.3 |
| 67 | 7.3 | 14.8 | 21.0 | 27.4 | 33.5 | 39.4 | 45.0 | 50.5 | 55.8 | 60.8 |
| 66 | 6.6 | 12.9 | 19.0 | 24.8 | 30.3 | 35.6 | 40.8 | 45.7 | 50.5 | 55.1 |
| 65 | 5.7 | 11.2 | 16.4 | 21.3 | 26.1 | 30.7 | 39.1 | 39.4 | 43.5 | 47.5 |
| 64 | 5.0 | 9.9 | 14.5 | 18.9 | 23.1 | 27.2 | 31.1 | 34.8 | 38.5 | 42.0 |
| 63 | 4.4 | 8.6 | 12.6 | 16.5 | 20.2 | 23.7 | 27.1 | 30.4 | 33.6 | 36.6 |
| 62 | 3.9 | 7.6 | 11.1 | 14.5 | 17.7 | 20.9 | 23.9 | 26.7 | 29.5 | 32.2 |
| 61 | 3.3 | 6.5 | 9.6 | 12.5 | 15.3 | 18.0 | 20.5 | 23.0 | 25.4 | 27.7 |
| 60 | 2.9 | 5.7 | 8.3 | 10.8 | 13.2 | 15.6 | 17.8 | 20.0 | 22.1 | 24.1 |
| 59 | 2.4 | 4.8 | 7.0 | 9.1 | 11.1 | 13.1 | 15.0 | 16.8 | 18.9 | 20.2 |
| 58 | 2.0 | 4.0 | 5.9 | 7.7 | 9.4 | 11.0 | 12.6 | 14.1 | 15.6 | 17.0 |
| 57 | 1.8 | 3.5 | 5.1 | 6.7 | 8.2 | 9.6 | 11.0 | 12.3 | 13.6 | 14.8 |
| 56 | 1.5 | 3.0 | 4.4 | 5.8 | 7.1 | 8.3 | 9.5 | 10.7 | 11.8 | 12.9 |
| 55 | 1.3 | 2.6 | 3.8 | 5.0 | 6.1 | 7.2 | 8.3 | 9.3 | 10.2 | 11.1 |
| 54 | 1.2 | 2.3 | 3.3 | 4.3 | 5.3 | 6.2 | 7.1 | 8.0 | 8.8 | 9.6 |
| 53 | 1.0 | 2.0 | 2.9 | 3.8 | 4.7 | 5.5 | 6.3 | 7.0 | 7.8 | 8.5 |
| 52 | 0.9 | 1.8 | 2.6 | 3.4 | 4.2 | 4.9 | 5.6 | 6.3 | 7.0 | 7.6 |
| 51 | 0.8 | 1.6 | 2.4 | 8.1 | 3.8 | 4.9 | 5.1 | 5.7 | 6.3 | 6.9 |
| 50 | 0.7 | 1.4 | 2.1 | 2.7 | 8.3 | 3.9 | 4.4 | 4.9 | 5.5 | 6.0 |
| 49 | 0.6 | 1.2 | 1.8 | 2.4 | 2.9 | 3.4 | 3.9 | 4.4 | 4.8 | 5.3 |
| 48 | 0.6 | 1.1 | 1.6 | 2.1 | 2.5 | 3.0 | 3.4 | 3.8 | 4.2 | 4.6 |
| 47 | 0.5 | 1.0 | 1.4 | 1.8 | 2.2 | 2.6 | 3.0 | 3.4 | 8.7 | 4.1 |
| 46 | 0.5 | 0.9 | 1.3 | 1.7 | 2.1 | 2.5 | 2.8 | 3.2 | 3.5 | 3.8 |
| 45 | 0.4 | 0.8 | 1.1 | 1.5 | 1.8 | 2.2 | 2.5 | 2.8 | 3.1 | 8.3 |

Figure 5:
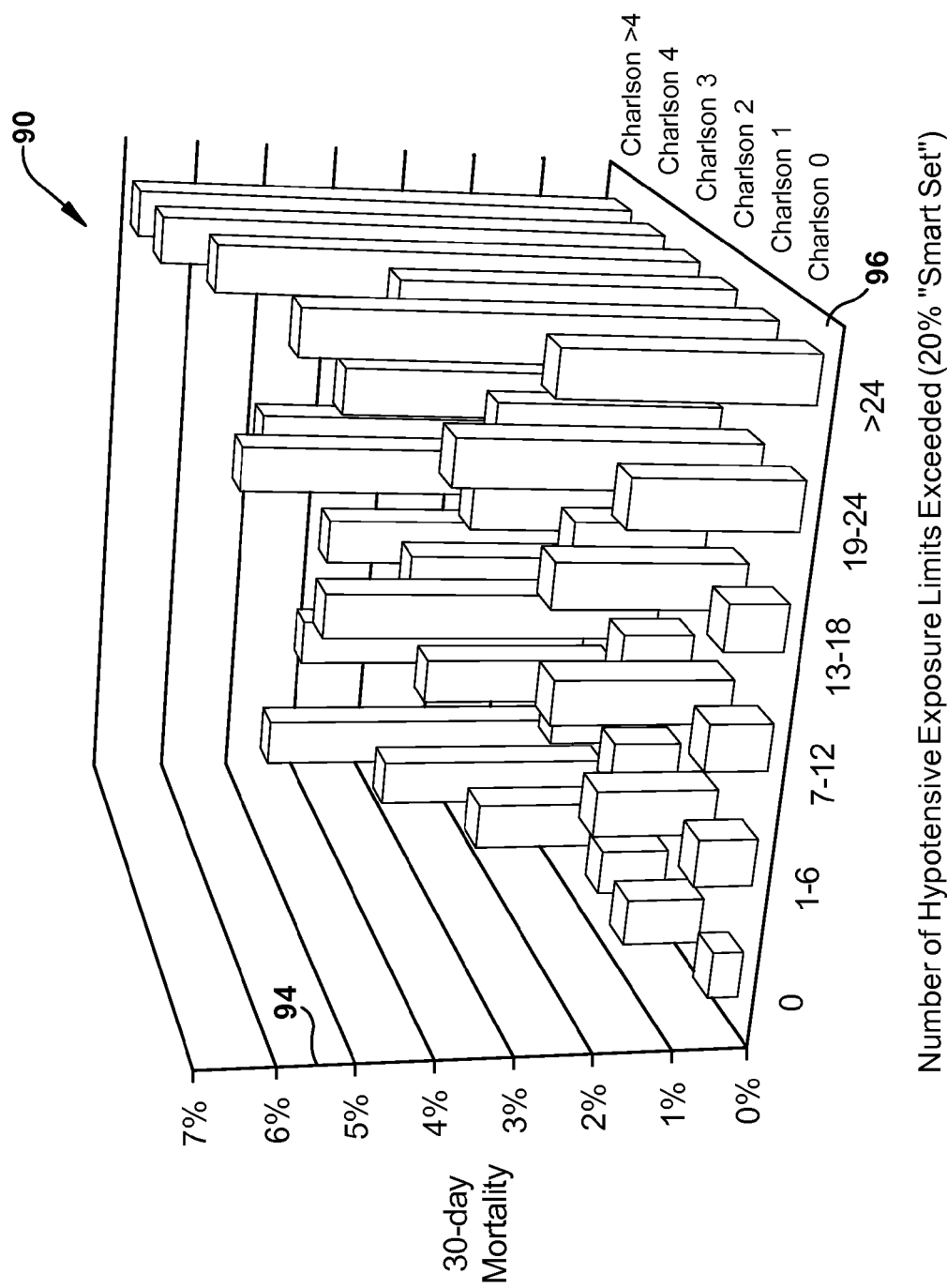
FIG. 5 is a chart illustrating a percentage likelihood of 30-day mortality for a patient as a function of a number of hypotensive exposure limits exceeded in the method of FIG. 4 and a Charlson Comorbidity Index.
Figure 8:
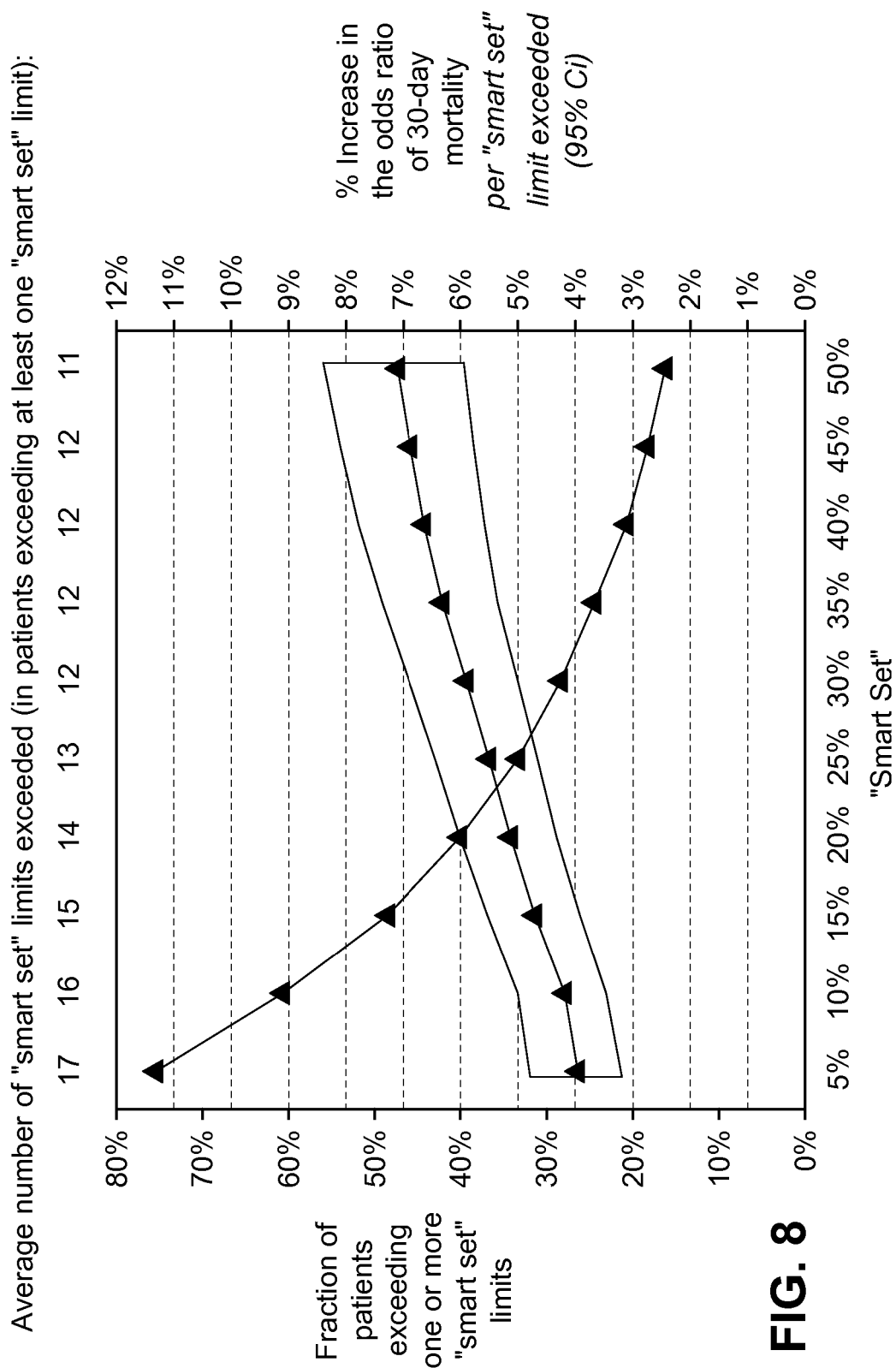

If none of the cumulative times exceed an associated exposure limit (N), the method returns to 74 to continue monitoring the biometric parameters. If an allowable exposure limit has been exceeded (Y), the method advances to 82, where a risk metric associated with the patient is updated to reflect an increase in a risk of patient morbidity or mortality. In one implementation, a risk index can be computed from this metric as an exponential function of the number of exposure limits that have been exceeded. For example, the risk index, $R_I$, can be calculated such that $R_I = R_B (1.05)^N$, where $R_B$ is a baseline risk for a given patient given a patient history and any other relevant physiological parameters measured, and N is the number of hypotensive exposure limits that have been exceeded (FIGS. 5 and 8). At 84, the anesthesiologist or practitioner caring for the patient is alerted and informed of the potential increase in risk to the patient. The method then returns to 74 to continue monitoring the biometric parameters.

FIG. 5 is a chart 90 illustrating a percentage likelihood of death within thirty days (30-day mortality) for a patient as a function of a number of hypotensive exposure limits exceeded in the method of FIG. 4 and a Charlson Comorbidity Index. In the chart, 30-day mortality is represented on a first axis 92, the number of hypotensive exposure limits exceeded is represented on a second axis 94, and Charlson Comorbidity Index is represented on a third axis 96. It will be appreciated from the chart that the number of hypotensive exposure limits exceeded is a significant predictor of 30-day mortality, particularly for healthy patients, that is, patients with a low (<3) Charlson Comorbidity Index. Further, looking at the effects of each independent variable 94 and 96 on the 30-day mortality when the other variable is at its lowest value, it appears that the number of hypotensive exposure limits exceeded provides at least as much discriminative power as the Charlson Comorbidity Index, considered a highly relevant predictor of patient outcome.

The inventors have performed some research to provide evidence-based guidelines on the effects of hypotension on procedural outcomes. Specifically, a study was designed to examine the relationship between intraoperative hypotension of varying severity and duration and 30-day postoperative mortality following non-cardiac surgery. To this end, the registries of Cleveland Clinic, of Hillcrest Hospital (a community hospital within the Cleveland Clinic Health System) and of Vanderbilt Medical Center were queried for data of 137,037 adult patients undergoing non-cardiac surgery. Intraoperative minute-to-minute mean arterial blood pressure (MAP) recordings were analyzed for periods of time spent below hypotensive thresholds ranging from 75 to 45 mm Hg. The association was sought between cumulative time spent below this array of thresholds and 30-day all-cause postoperative mortality derived from the Social Security Master Index. Extracted information included patient demographics (e.g., age, gender), a Charlson co-morbidity score, derived from the patients' list of pre-existing diagnoses (problem list ICD-9 codes), a type of anesthetic, a case duration, a cumulative amount of documented blood loss, minute-to-minute mean arterial blood pressure (MAP) values, and all-cause mortality within 30 days of surgery, originating from the U.S. Social Security Death Index Master File. Preoperative hypertension was determined according to the presence of any one of several ICD-9 codes (401.xx; 402.xx; 403.xx; 404.xx; or 405.xx).

For each minute of every case, patients' effective MAP was considered to have been the larger of the most recent automatically-acquired non-invasive MAP value (obtained within the immediately preceding five minute period) or the most recent invasive MAP value acquired contemporaneously (continuously recorded at one-minute intervals), rejecting values less than 30 mm Hg as likely artifacts. For every patient, the cumulative periods of time were calculated for which the effective MAP was below each one of an array of hypotensive thresholds ranging from 75 to 45 mm Hg, using SQL Management Server 2008 and EXCEL 2010 with VBA (Microsoft Corporation, Redmond, Wash.). Multivariable logistic regression (UNISTAT 6.0, London, UK) was employed to ascertain within a development subset of patient records (35,904 patients, undergoing surgery on Cleveland Clinic's main campus between Jan. 1, 2009 and Sep. 30, 2010) any factors significantly (p<0.05) associated with increased 30-day mortality, including the respective amounts of time spent below each of the MAP thresholds between 75 and 45 mm Hg. As a result, arrays of hypotensive exposure limits (for cumulative time spent below each of these MAP thresholds) were identified that were associated with a certain percent increase in the odds ratio for 30-day mortality, ranging from 5% to 50% ("smart sets").

The validity of these new "smart sets" in portending adverse outcome was subsequently further assessed in an additional 101,133 patient records from three different care settings (44,476 patients from Cleveland Clinic main campus, undergoing surgery between Oct. 1, 2010 and May 31, 2012; 27,610 patients from Hillcrest Hospital undergoing surgery between May 2010 and May 2013; and 29,047 patients from Vanderbilt Medical Center, undergoing surgery between January and December, 2011), by comparing their cumulative intraoperative hypotensive exposure times against each of these "smart set" limits and examining the 30-day survival rates of patients exceeding these limits with those of patients not exceeding these limits.

Figure 6:
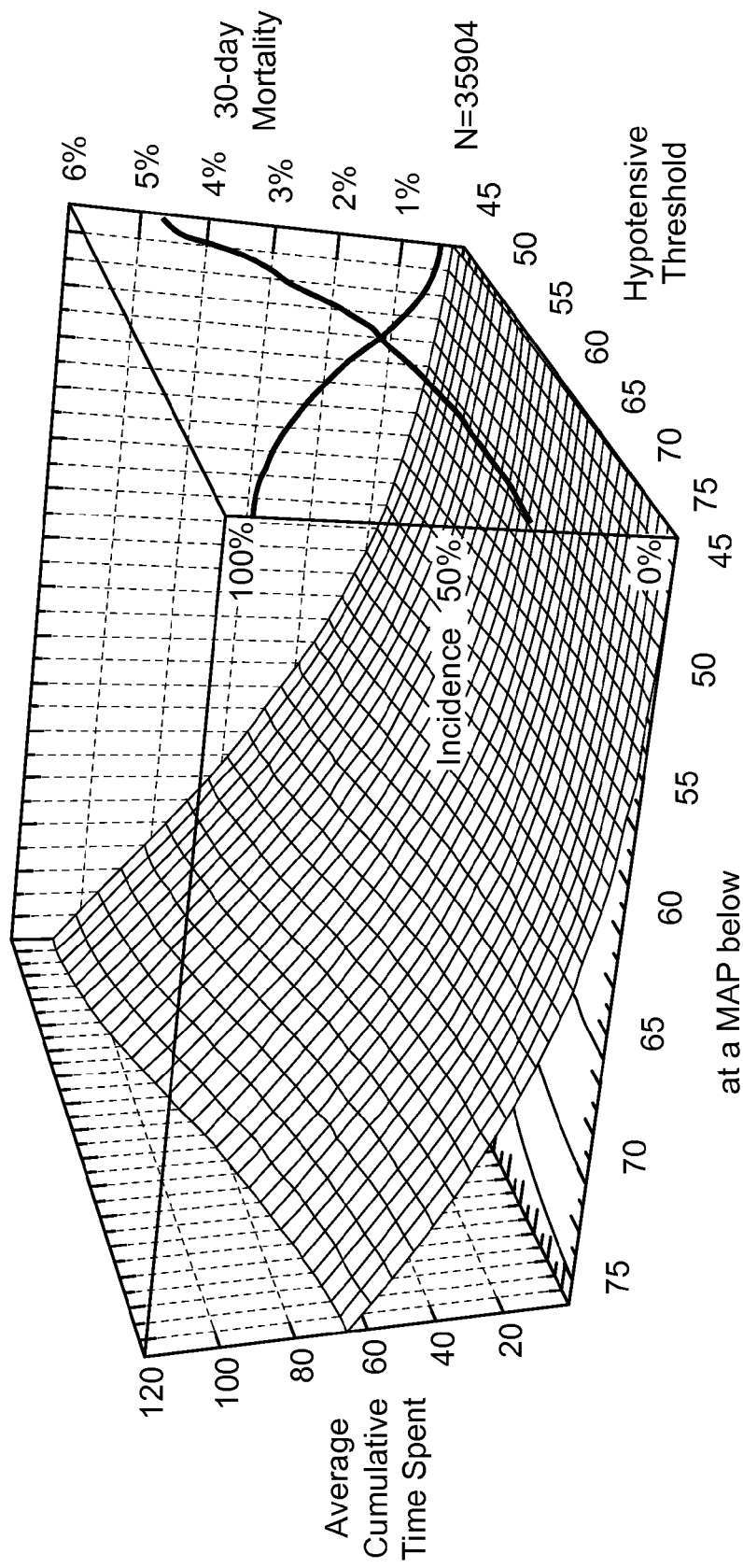
FIGS. 6-11 illustrate the results of a study of the effects of hypotensive thresholds on patient outcomes from procedures under anesthesia.

Specifically, of 44,968 cases retrieved from Cleveland Clinic's main campus between Jan. 1, 2009 and Sep. 30, 2010, a complete set of data was obtained for 35,904 cases of patients who survived the intraoperative period and experienced an overall all-cause 30-day mortality of 2.1%. The average case duration was 204 minutes (range 5-1169), with anesthetic techniques consisting of inhalational anesthesia (82.9%), intravenous anesthesia (7.2%), spinal (4.9%), epidural (0.9%), peripheral nerve block (0.3%) and monitored anesthesia care (3.9%). Intraoperative hypotension was common, with MAP dropping (for at least one minute) below 75 mm Hg in 92% of cases and below 45 mm Hg in 10% of cases (FIG. 6). Dropping below a certain MAP threshold caused accumulation not only of time spent below that particular threshold but of varying average amounts of time spent below each of the other MAP thresholds in the array above and below (the more time the higher the threshold and vice versa, FIG. 6). Worsening hypotension (any amount of time spent below progressively lower MAP thresholds) was reflected by a progressive increase in the average cumulative amounts of time spent below each of the other thresholds across the entire array of MAP thresholds and, associated with this, a progressive increase in 30-day mortality (FIG. 6). Preliminary multivariable logistic regression identified patient age (1.043, 1.037-1.049, per year), Charlson co-morbidity score (1.193, 1.161-1.227, per increment) and cumulative amount of blood loss (adjusted odds ratio of 1.038, 1.027-1.049, per 500 ml) as independent predictors of 30-day mortality. All subsequent analyses involving MAP were adjusted for these factors as well as case duration.

Figure 7:
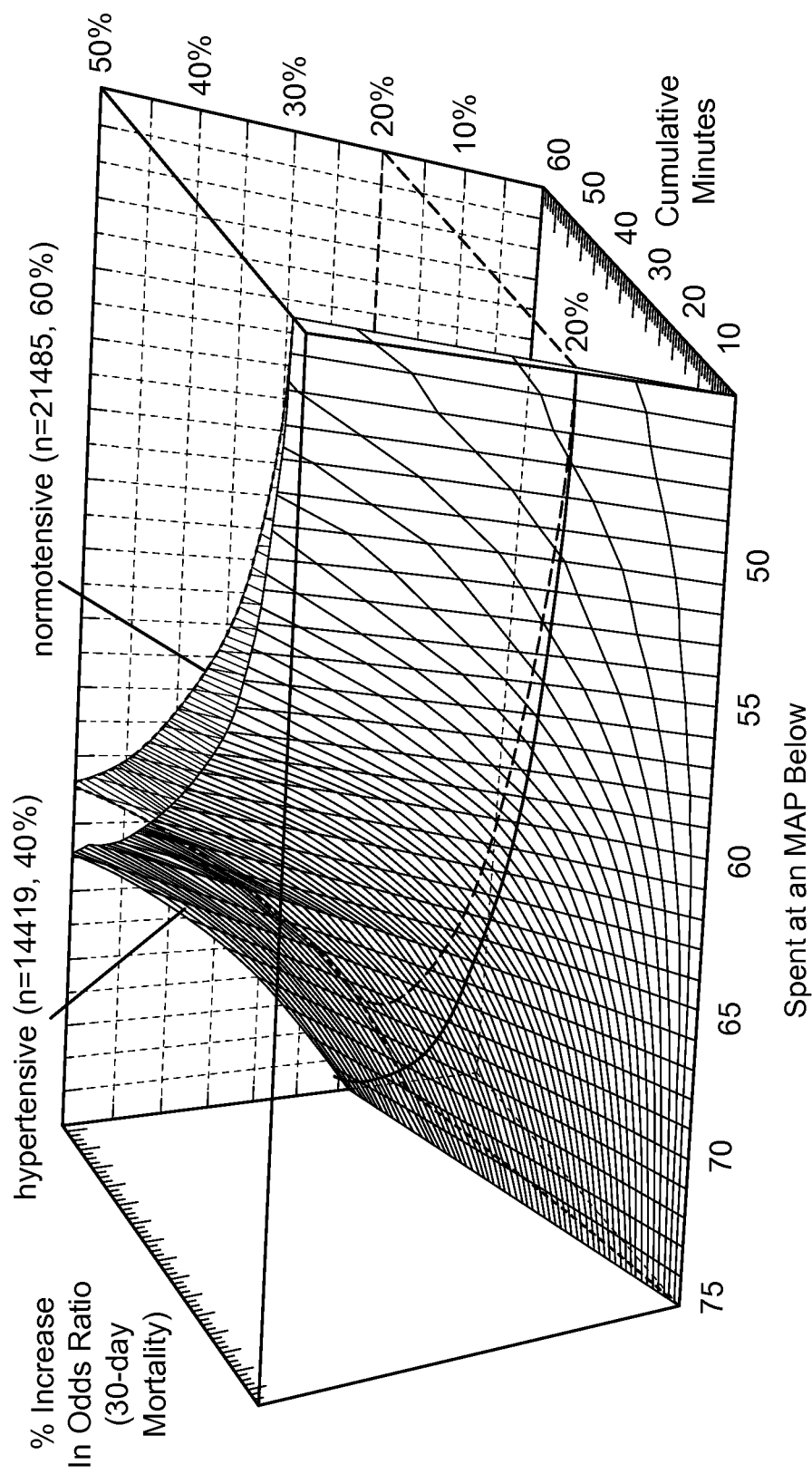

The relationship between the severity of hypotension (the hypotensive MAP threshold exceeded), the cumulative amount of time spent below that threshold and adjusted odds of 30-day mortality is depicted in FIG. 7. As demonstrated in the figure, the cumulative amount of time spent below each of the various MAP thresholds was independently associated with an increased odds ratio for 30-day mortality. Furthermore, dropping below progressively lower MAP thresholds had a progressively greater adverse association with 30-day mortality per unit of time accumulated below that threshold. For any given MAP threshold, patients carrying a preoperative diagnosis of hypertension (prevalence of 40% according to the definition above) required less cumulative time to be accrued below that threshold to incur the same increase in 30-day mortality odds ratio as patients without a history of hypertension. The resulting cumulative exposure times below each of the MAP thresholds (in minutes) that corresponded to the same respective increases in the odds ratio of 30-day mortality ranging from 5% to 50% (risk-based "smart sets") are listed in Tables 1 and 2.

Figure 9:
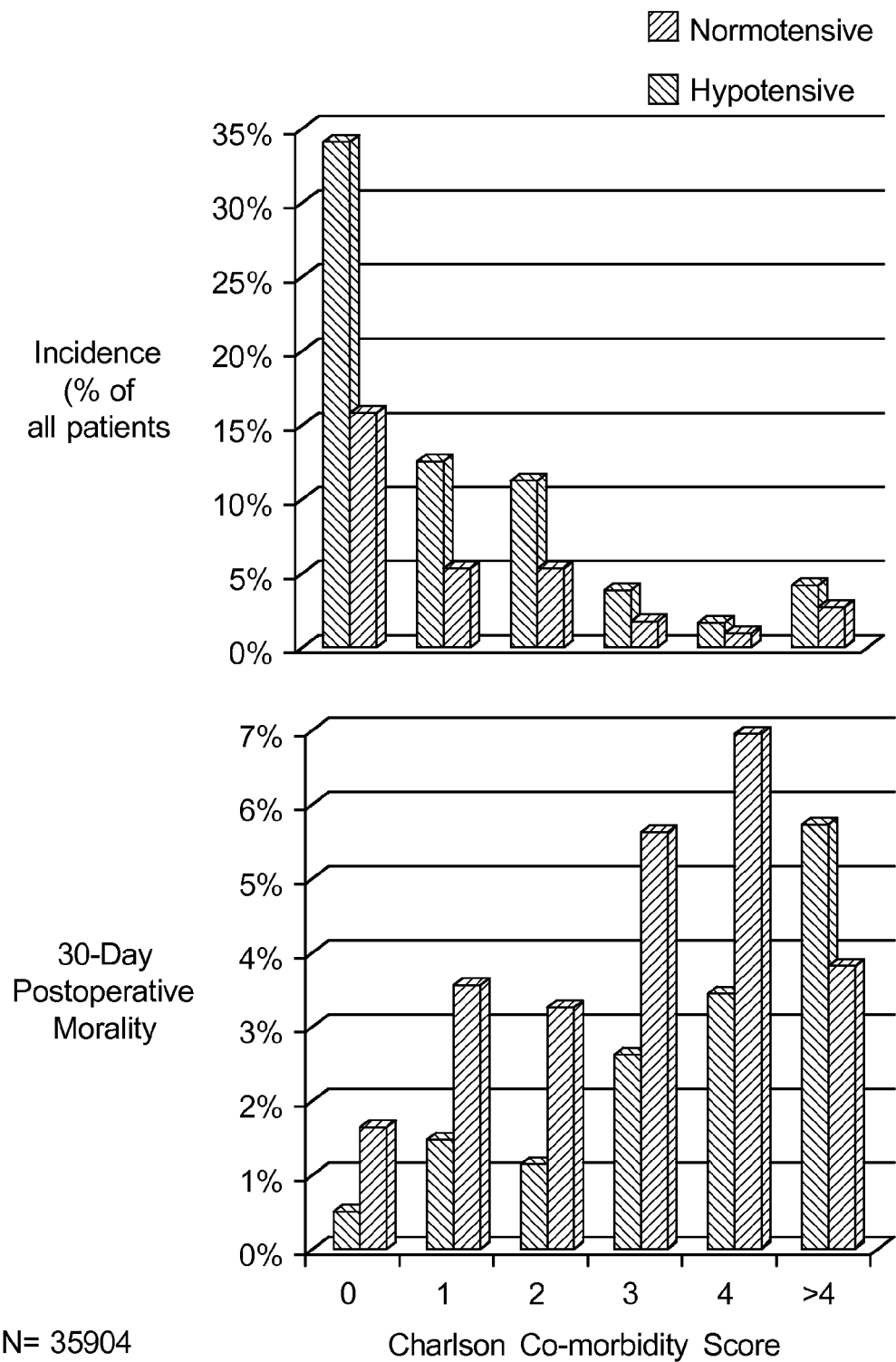

Within each of these "smart sets", the total increase in mortality attributable to hypotensive exposures for any given patient depended upon the total number of exposure limits exceeded within the "smart set", with each incremental limit exceeded portending a compounding 5-7% further increase in the odds ratio for 30-day mortality (FIG. 8). The average number of exposure limits exceeded within the various "smart sets" ranged from 17 in the 5% "smart set" to 11 in the 50% "smart set" (FIG. 8). The adverse effect of hypotensive exposures on 30-day survival was independent of and adjusted for the Charlson co-morbidity score. However, there was a significant statistical interaction between hypotensive exposures and the Charlson co-morbidity score: while a greater Charlson co-morbidity score portended overall progressively greater 30-day mortality, the relative (i.e., percent) increase in mortality of patients exceeding "smart set" limits was inversely associated with the co-morbidity score (Wald test, Bonferroni adjusted, $p<0.05$), suggesting that the more prevalent "healthier" patients with co-morbidity scores between 0 and 3 were affected more extensively than less prevalent "sicker" patients with a co-morbidity scores of 4 or greater). This is shown in FIG. 9 for patients either exceeding or not exceeding any one or more of the 20% "smart set" limits.

Figure 10:
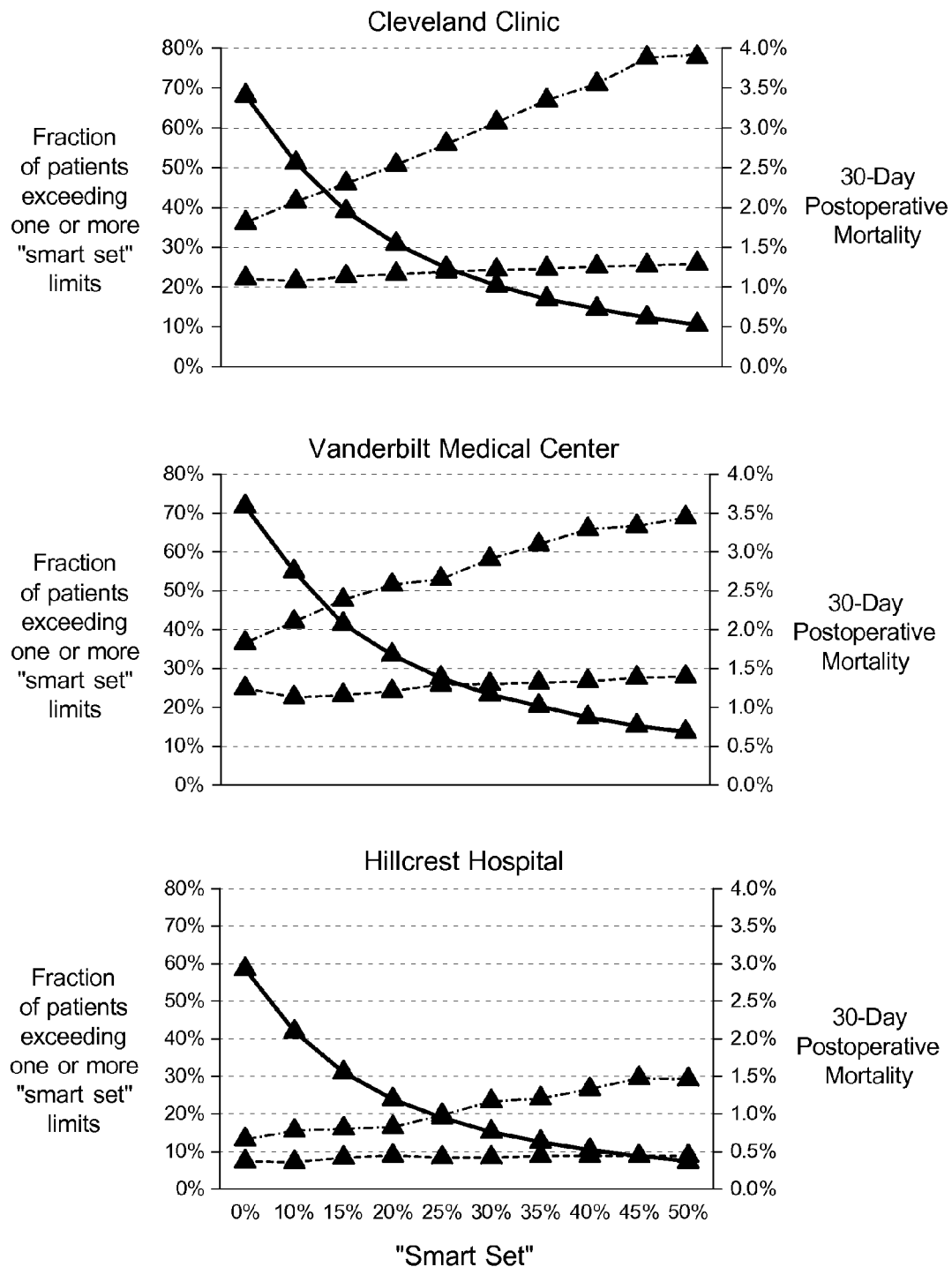

In the additional 101,133 patients examined, hypotensive exposures were compared to each of the various risk-based "smart set" limits depicted in Tables 1 and 2, choosing the limits according to whether or not patients carried a history of hypertension. The fraction of patients exceeding any one of the exposure time limits ranged between 59-72% (5% "smart set") and 8-14% (50% "smart set") and was similar between the three institutions tested (FIG. 10, dark lines). While the overall 30-day mortality was also similar at the Cleveland Clinic main campus (1.6%) and at Vanderbilt Medical Center (1.7%), and was greater than that at Hillcrest Hospital (0.5%), those patients exceeding "smart set" limits exhibited a similar progressively greater, more than doubling of 30-day mortality in each one of the three care settings (FIG. 10, upper light lines) compared to those patients not exceeding any of these "smart set" limits (FIG. 10, lower light lines).

Figure 11:
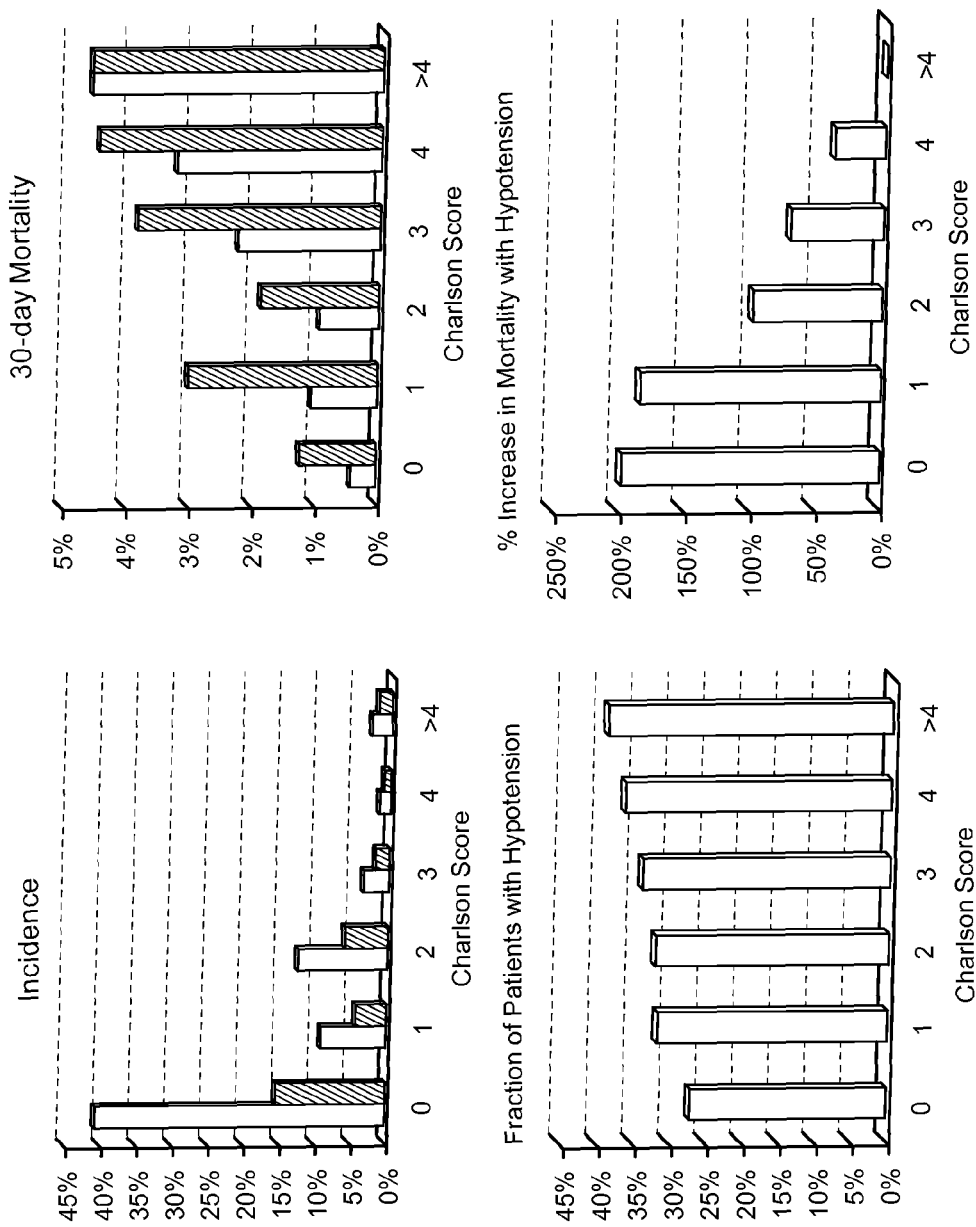

When examined in 94,351 of these 101,133 patients for which a Charlson co-morbidity score could be obtained from the available data set, an inverse relationship was confirmed between the increase in mortality and the Charlson co-morbidity score of patients exceeding (an average 12.9) exposure limits of the 20% "smart set" (FIG. 11). When being stratified according to the number of "smart set" limits exceeded (0; 1-6; 7-12; 13-18; 29-24; >24), there was a progressive increase in mortality with the number of "smart set" limits exceeded (FIG. 5). This association was most pronounced in the majority (93%) of healthiest patients with a co-morbidity score below 3 (FIG. 5).

This study has demonstrated that periods of intraoperative hypotension which exceeded certain sets of cumulative exposure time limits were indicative of progressively increased 30-day mortality following non-cardiac surgery and routinely encountered in a substantial fraction of patients, primarily affecting healthier rather than the very sickest patients. Hypotensive exposures may thus a represent a conceivably controllable factor contributing to compromised long term outcome in a significant fraction of surgical patients. While it is commonly accepted that severe hypotension is poorly tolerated, the inventors have determined that longer-term outcomes may also be affected by extended periods of less severe hypotension in patients surviving the immediate perioperative period. However, relatively little had been known about the acceptable blood pressure ranges below which anesthesia providers should be concerned not only about getting patients through the surgery alive (and without major intraoperative complications), but also about minimizing any potential longer term adverse outcome. Efforts to date had been largely concerned with trying to identify and avoid hypotension below some distinct blood pressure threshold deemed to be critically low, consistent with the design limitation of conventional blood pressure monitors which typically lack the ability to alert providers to anything but the most recent reading falling below a certain adjustable threshold.

In contrast to conventional vital sign monitors, modern electronic anesthesia information systems can be adapted as described herein to realize the promise the potential of more sophisticated clinical decision support (DSS) functionality by being able to take into consideration more comprehensive information in real time, including pertinent pre-existing conditions (such as a history of hypertension) as well as both the severity and duration of patients' deviation from certain acceptable vital sign ranges over the course of an entire case. A desirable feature of the described systems and methods is the use of "smart" alarms designed to detect and alert providers to certain levels of risk for adverse postoperative outcome attributable to such deviations in vital signs that may be amenable, to some extent, to control by anesthesia providers. The study described herein was designed to test the hypothesis that postoperative outcome may be associated not only with the severity of hypotension but also the duration of hypotensive periods of time spent below a range of mean arterial blood pressure (MAP) thresholds that are commonly encountered during anesthesia.

The present data demonstrate a significant independent association between the cumulative times accrued below a wide range of MAP thresholds commonly experienced during non-cardiac anesthesia (and not usually considered to be of concern by most anesthesia providers) and increased all-cause mortality within 30 days after surgery. This association appears to affect a considerable fraction of patients (such as one in every three patients for the 20% "smart set"), to not be focused on patients with high comorbidity but rather affect the majority of patients with lower co-morbidity scores, and to similarly apply to both major academic medical centers as well as a community hospital (even if the absolute 30-day mortality rates were different in these care settings).

Consistent with the existing literature, which has not been able to identify any clinically meaningful threshold for hypotension, there does not seem to have been one particular blood pressure threshold having to be dropped below to portend a greater risk for 30-day mortality versus being spared from such an effect. Rather, increased risk appears to have been related to an interaction between severity and duration of hypotension below a wide range of commonly encountered MAP thresholds. In this sense, "smart set" limits appear to be somewhat analogous to diving charts, suggesting that less time may be permissible to be spent at a lower MAP (a greater depth) while incurring a similar amount of risk. The present data suggest that risk does not appear to be sufficiently quantified by examining time accrued below just one MAP threshold but rather below a wide range of commonly encountered MAP thresholds.

Varying limits of cumulative exposure time need to be exceeded below these various MAP thresholds to incur an equivalent increase in risk, each of these time limits being different for patients with or without a preoperative diagnosis of hypertension (FIG. 9 and Tables 1 and 2).

This particular type of approach to identifying acceptable blood pressure thresholds is facilitated by the increasing availability of electronic anesthesia information systems. With the arrival of clinical decision support (DSS) functionality that offers nearly instantaneous access to all required information it is conceivable that notification to such increased risk based on progressive hypotensive exposures can be made available to the anesthesia provider in near real time.

While hypotension might theoretically be escaped altogether by minimizing the time a patient's MAP is permitted to drop below 75 mm Hg, this would be neither feasible in the reality of clinical practice nor likely desirable. In the present study, over 90% of patients' MAP dropped below 75 mm Hg at some point during their anesthetic. However, only approximately one third of patients did so long enough to exceed at least one of the 20% exposure limits (FIGS. 8-10). The conceivable benefit of DSS providing the suggested type of "smart alerts" in real time is that these would allow permissive hypotension to be instituted whenever indicated (such as to minimize bleeding) without invariably causing the triggering of notifications (as would be the case with traditional devices) while still keeping track of cumulative times spent in a hypotensive state and providing notification only to provider-selectable increments of risk resulting from more prolonged periods of hypotension. Patient benefit might be derived from minimizing apparently hazardous periods that may be spent gratuitously at a MAP between 60 and 70 mm Hg, a pressure range traditionally considered only mildly hypotensive and not generally viewed as posing a problem for the patient.

These data further suggest that patients may be readily detectable as being at an increased risk for adverse 30-day postoperative outcome and may thus possibly be prioritized for more intensive follow-up care by the time they leave the operating room theater on the basis of the total number of risk-based "smart set" limits that were exceeded over the course of their surgical procedure. Contrary to conventional belief such hypotensive exposures appear to not be limited to the sickest patients with the very highest co-morbidity scores but are similarly prevalent across all patients undergoing anesthesia. Furthermore, also contrary to conventional belief, the adverse impact of hypotensive exposures appear to be most pronounced in the large majority of (>85%) of healthiest patients with lower comorbidity scores and may thus represent a potentially preventable factor threatening the best outcome of large numbers of otherwise lower risk patients whose increase in their count of "smart set" limits exceeded may be detected in real time and consequently prevented from further progression.

Figure 12:
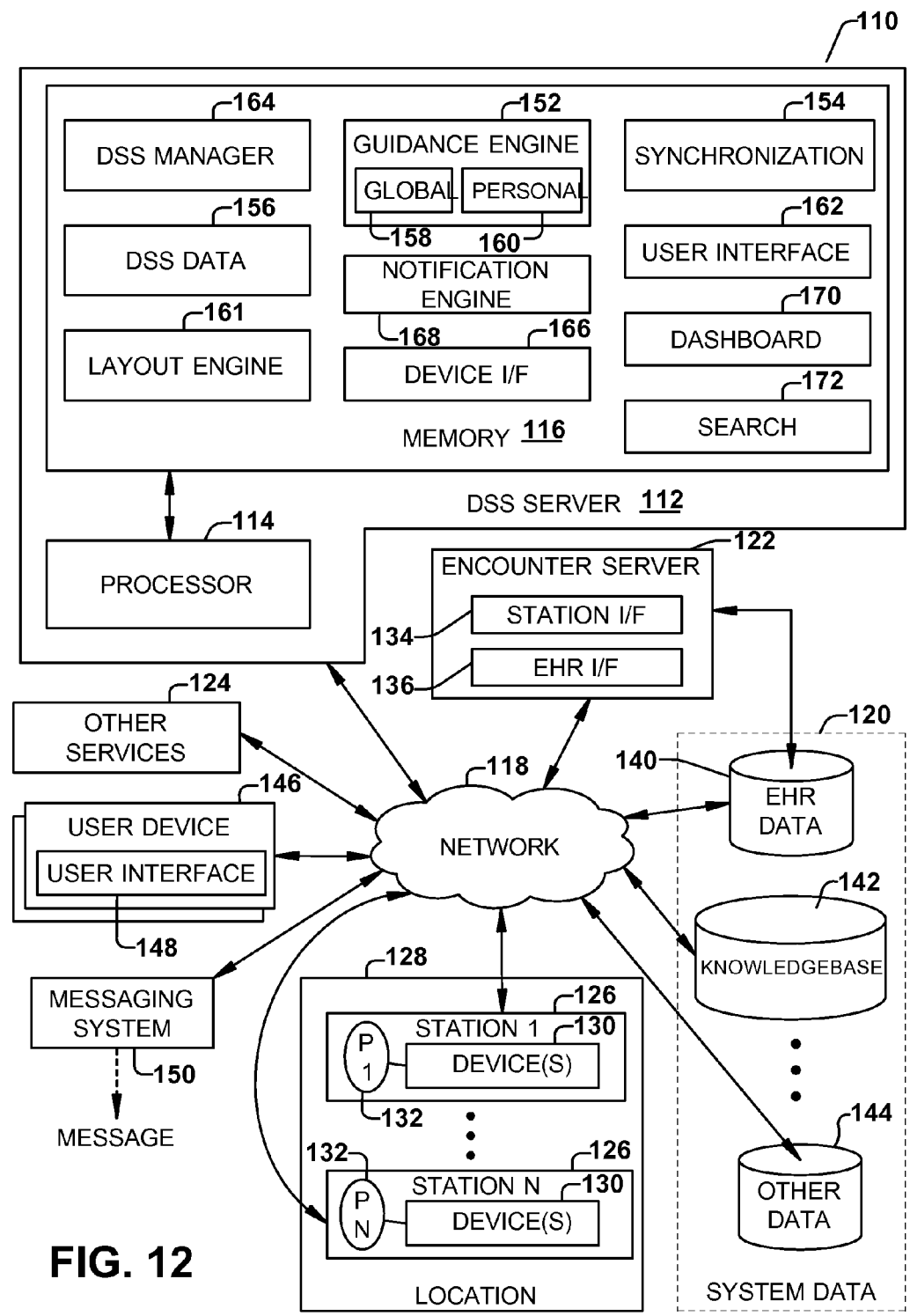
FIG. 12 depicts an example of a decision support system that might implement systems and methods in accordance with an aspect of the present invention.

FIG. 12 depicts an example of a decision support system (DSS) 110 that might implement systems and methods in accordance with an aspect of the present invention. In the example of FIG. 12, the DSS 110 includes a DSS server 112. The server can include one or more processor 114 and memory 116. The memory can store data and machine readable instructions that can be executed by the processor 114. For example, the memory 116 can comprise physical memory, such as can reside on the processor 114 (e.g., processor memory), random access memory or other physical storage media (e.g., CD-ROM, DVD, flash drive, hard disc drive, etc.) or a combination of different memory devices that can store the machine readable instructions. The memory 116 further can be implemented within a single machine, as depicted in FIG. 12, or it can be distributed across multiple machines. The data utilized for implementing the systems and methods described herein can also be stored in the memory 116 or in some other arrangement of one or more memory structures that are accessible for use by the system 110.

The DSS server 112 can be connected to a network 118 such as to provide for communication between the DSS server and various services, devices and data stores that can collectively form the system 110. The network 118 can be a local area network, a wide area network, or a combination of different various network topologies, which may include physical transmission media (e.g., electrically conductive, optical fiber media or the like) and/or wireless communications media, that can be utilized for communicating information. The network or at least a portion of the methods and functions implemented thereby can operate in a secure manner (e.g., behind a firewall separated from public networks) and/or utilize encryption for data communications.

In the example of FIG. 12, the DSS server 112 can employ the network 118 to access system data 120, an encounter server 122, as well as one or more other services generally indicated at 124. These other services 124 can correspond to various other servers that can store and provide information pertinent to a given patient encounter or to a patient's health condition, more generally. For example, these services can be used to retrieve patient data that may be useful in determining appropriate cumulative exposure time thresholds for various physiological parameters for use in a procedure under anesthesia, such as, for example, a history of hypertension. Such other services 124 may also execute methods and functions that can be utilized by the DSS server 112, such as via corresponding application interfaces (APIs). The particulars of such other services 124 can vary according to the particular purpose of the DSS 110.

The DSS server 112 can obtain information from a plurality of stations 126, demonstrated as station 1 through station N, where N is a positive integer denoting the number of stations. The stations 126 can be associated with one or more locations 128. For example, the location 128 can correspond to a portion of a facility (a floor, a ward or the like), a facility itself or a plurality of different facilities for which the DSS 110 can be configured to provide clinical decision support.

In the example of FIG. 12, each station 126 can include a number of one or more devices 130. Each of the devices 130 can be associated with a given patient 132, demonstrated as Patient P1 through Patient PN. Thus in this example each station 126 can include a given patient, although it is understood that more than one patient could be associated with a given station in other situations. The DSS 110 can be configured to provide decision support for any number of one or more patient encounters, such as a procedure requiring general anesthesia. As used herein a patient encounter corresponds to a record that is maintained by the DSS 110 for each patient 132 during a time period for a given visit, such as can include their time for which they were monitored in a given station 126 (e.g., a perioperative period).

The devices 130, for example can obtain real time information about a patient condition that can be monitored during each active patient encounter. Such real time information can include, for example arterial blood pressure, including mean arterial blood pressure, venous blood pressure, heart rate, temperature, respiration rate, pulse oximetry as well as any other parameters that may be pertinent to the health condition of a patient during the encounter. The DSS server 112 can obtain information directly from such devices 130. Alternatively or additionally, the DSS server can obtain corresponding patient data for the encounter server 122 that may collect and process information from one or more of the devices 130.

As an example, the encounter server 122 can include a station interface 134 that can be utilized to acquire information from one or more of the devices 130. The encounter server 122 can obtain such data at a desired sample rate that might vary according to the type of information, such as depending on the rate that each of the devices samples such data. For example, blood pressure readings may be performed by a blood pressure monitor every five minutes whereas pulse oximetry or heart rate will be sampled at much higher rates. It will be appreciated that these rates will vary according to the specifics of a patient encounter. For example, during a procedure utilizing general anesthesia, more frequent measurement of various biometric parameters, including arterial blood pressure, may be performed. The encounter server 122 can store information from such devices 130 data as part of a patient encounter in memory associated with the encounter server.

The encounter server 122 can also include an electronic health record (EHR) interface 136 that can be utilized to retrieve patient information from an EHR database 140. For example, the encounter server 122 can employ the EHR interface 136 to pull patient encounter data, as well as other pertinent patient records from the EHR database 140 (e.g., patient demographic information, patient medical history, or the like). The DSS server 112 can employ also the encounter server (e.g., as middleware) 122 to obtain relevant patient information from the EHR database, such as via an encounter interface (e.g., an API). The encounter server 122 can also be programmed to store relevant encounter data back to the EHR database 140.

In addition to health record data that may be stored in the EHR database 140, the DSS server 112 can also access a knowledgebase 142 or one or more other data sources, indicated at 144. The knowledgebase 142 can be utilized to access a variety of reference texts, medical publications, guidelines, policies and procedures and care algorithms that may be utilized by users of the system 110. The DSS server 112 can make such information available to its users via dynamic or configurable links. As an example, the DSS server 112 can present patient encounter information to a user via one or more web pages that contain dynamic links (e.g., hypertext links) to predefined resource locations (e.g., uniform resource locations (URLs)) at which pertinent information corresponding to the system data 120 can be provided. As described herein, the DSS server 112 can be programmed to automatically select the information according to the real-time conditions of the patient, preferences of the user and other information related to an event that is occurring at a given one of the respective stations 126. The DSS server 112 can provide an encounter GUI that is populated with such selected information and/or links to such information.

In the examples described herein, the DSS server 112 can be implemented in a context of a perioperative patient management system. For instance, the DSS server 112 can provide timely patient encounter information, guidance and alerts to users so that informed decisions can be made in a time-critical environment. As mentioned above, data specific to each active patient encounter (associated with the respective station 126) can be acquired by the DSS server 112 from a variety of sources, such as including the encounter server 122, EHR data 140, the knowledgebase 142, other data sources 144 and/or other services 124 that may provide pertinent information for the decision support process for each active patient encounter.

Authorized users can employ a corresponding user device 146 to access information generated by the DSS server 112. There can be any number of user devices 146 that can access the information from the DSS server 112. A given user device 146 can include a user interface 148 that allows the user to access the functions and methods implemented by the DSS server 112 as well as to retrieve related content information. The user interface 148, for example, can include a web browser (or a thin client application) that can be provided dynamic links for accessing the functions and methods corresponding to the DSS server 112. It is to be appreciated that such user device 146 can be a computer, a work station, as well as a mobile device (e.g., a smart phone, laptop or tablet computer) that can run a corresponding application for accessing the functions and methods associated with the DSS server. The user device 146 can be located in a corresponding station (e.g., in a OR) 126 as well as can be implemented as a remote device, that can access the information produced by the DSS server 112, such as by accessing corresponding screens via embedded web browser controls.

The DSS server 112 can also employ a messaging system 150 to send messages to respective users. For example, the user device 146 can also be a pager to which one or more alphanumeric messages can be sent from the DSS server via the messaging system 150. In this example, the messaging system 150 can correspond to a hospital paging system. The messaging system 150 can also be implemented as a text messaging system, an automated phone messaging system, and/or an email or text messaging system for providing corresponding messages to respective users.

The DSS 110 can also provide alerts, other notifications and relevant information, corresponding to patient conditions that are monitored by the DSS, to the users that can be received via the user device 146, including the various alerts representing a hypotensive state exceeding exposure limits for various mean arterial blood pressure thresholds, as described previously. As further described herein, alerts can correspond to global types of guidance. Additionally, or alternatively, the DSS server 112 can be configured by a given user to provide personalized alerts and guidance to the given user. As a result, the system 110 can be customized according to the individual preference of a given user.

Individual users having supervisory control or similar authorization may also be able to configure global types of guidance and global alerts that will be provided to users in the system. In this way, the DSS 110 can help improve patient outcomes, such as by reducing mistakes, reducing potential oversights and providing a mechanism for more timely recognition of conditions that may require user intervention, such as prolonged hypotensive exposures as described above. The DSS 110 can also facilitate on-demand learning by offering tools for investigating information pertinent to a given patient condition via links automatically generated for an active patient encounter from the knowledgebase 142 or the other data 144.

The DSS server 112 can include a guidance engine 152 programmed to evaluate information and data pertinent to the evolving patient condition for each active encounter in a given station 126. As mentioned above, the guidance engine 152 can receive the patient encounter data from various devices 130, which may be directly monitoring patient's conditions, as well as from data available from other sources such as the system data 120, the encounter server 122 and other services 124. The guidance engine 152 can analyze such information and compute decision support data that can be presented to a user in the form of real-time assistance. The guidance engine can also search the system data 120 or other sources for pertinent patient information, guidelines and procedures relevant to current circumstances of the active patient encounter. Data acquired by the DSS server 112 for each station 126 can be stored in the memory 116 or another database, such as may be part of the system data 120.

As a further example, the DSS server 112 can include a synchronization module 154 that can be utilized for sampling data from the encounter server 122 as well as from each of the stations 126 and other services 124 that may be associated with monitoring patient conditions. As one example, a programmable sampling time period can be specified for timing retrieval of information by the synchronization module 154 of the DSS server and other services, such as the encounter server 22 during which the DSS server, via the synchronization module 154, can retrieve information. For instance, a mutually agreed upon time such as between the 15th and 50th second of each minute can be set and programmed into the synchronization module to minimize disruption with the ongoing activity of the encounter server 122.

Examples of some conditions that can be monitored by the devices 130 at each station 126 can include: EKG, pulse oximetry, blood pressure, temperature, respiration rate, or other parameters that can be monitored directly from the patient. Additional information can be obtained from the devices 130 such as composite parameters based upon several independent parameters, for example a "triple Low" condition defined as a low bi-spectral index (BIS), mean arterial pressure (MAP), end-tidal anesthetic concentration (MAC). Alternatively, this and other information and parameters can be computed by the DSS server 112 based on data retrieved from any of the data sources.

As a further example, the following table demonstrates a sample set of data parameters that can be acquired by the DSS server 112 and where such parameters may be obtained for an embodiment, based on which decision support and guidance can be provided:

TABLE 3

| Parameter | Data Source |
|---|---|
| Airway Summary | Encounter Parameter Data |
| Allergies | Encounter Parameter Data |
| Anesthesia Type | Encounter Parameter Data |
| ARKS Bolus Meds | Encounter Bolus Meds |
| Arterial Diameter | Encounter Monitor Data |
| Arterial Heart Rate | Encounter Monitor Data |
| Arterial Mean | Encounter Monitor Data |
| Arterial Sys | Encounter Monitor Data |
| BIS | Encounter Monitor Data |
| CO2 | Encounter Monitor Data |
| CVP | Encounter Monitor Data |
| Desflurane | Encounter Monitor Data |
| dPP | Other Data |
| dPP2 | Other Data |
| EHR Medical History (ICD-9 code) | EHR database |
| EPIC Medications | Encounter Medications |
| Fi O2 | Encounter Monitor Data |
| HR | Encounter Monitor Data |
| Isoflurane | Encounter Monitor Data |
| Mech Min Vol | Encounter Monitor Data |
| Medical History | Encounter Parameter Data |
| NBP Dia | Encounter Monitor Data |

TABLE 3-continued

| Parameter | Data Source |
|---|---|
| NBP Mean | Encounter Monitor Data |
| NBP Sys | Encounter Monitor Data |
| Patient Position | Encounter Parameter Data |
| Regional Block Type | Encounter Parameter Data |
| Sevoflurane | Encounter Monitor Data |
| Sp O2 | Encounter Monitor Data |
| spO2 Variability | Encounter External Data |
| Temp 1 | Encounter Monitor Data |
| Temp 2 | Encounter Monitor Data |
| Warming Devices | Encounter Parameter Data |

In Table 3, the data sources including the term "Encounter" can be obtained from the encounter server. Further, it will be appreciated that any of the parameters listed above can be utilized in determining patient specific thresholds and exposure limits for a given patient, as well as features, along with the measured cumulative time below each threshold, for a predictive model of post-procedure morbidity or mortality.

The guidance engine 152 can be utilized to provide passive guidance, active guidance as well as a combination of passive and dynamic guidance to a user via a user device. The passive guidance can correspond to presenting the information directly as obtained from a device, such as can be presented on a user device 146 in the form of text, graphics or a combination of texts and graphics showing various patient conditions such as vital sign trends. The passive guidance can also include links to pertinent information that can be obtained from the system data 120 or other services, such as links to various documents that may be relevant to the patient's 132 evolving condition, patient history or other information that can be obtained for an active patient encounter from the system data 120. This may include a search module 172 that can be utilized to identify and locate content pertinent to a given patient encounter. The search module can provide the content directly or via hypertext links or otherwise. For example, the search module 172 can correspond to a commercially available or proprietary search engine that can be utilized to query the system data 120 or other resources for information and guidance that may be pertinent to the patient condition based upon the encounter data or a patient history data. For example, the search module 172 can query any number of one or more databases and such queries may be run periodically in response to the evolving data that is collected by the DSS server for each patient encounter.

Individual instances of the search module 172 thus can be utilized for each patient encounter for retrieving pertinent information for each respective patient. In addition to implementing such queries in response to the real-time information, such data can be analyzed (e.g., by the guidance engine 152) to detect trends or time varying parameters that may indicate specific conditions for which the search module can in turn locate relevant information that is presented to the user via the encounter GUI. Thus as described herein, the search module 172 may employ the results of expressions implemented by the guidance engine to implement corresponding searches such that the information being presented to the user at a given user device 146 is timely and relevant to the patient's current and evolving condition.

As a further example, the guidance engine 152 can be programmed to provide guidance, including dynamic or passive guidance, in response to detecting an adverse condition associated with a patient. For example, the guidance engine 152 can retrieve pertinent passive information (e.g., documents, procedures, or the like) in response to detecting a vital sign or other indication of an adverse patient condition for a given patient 132. The alert provided when a patient's cumulative time spent below a given mean arterial blood pressure threshold exceeds the acceptable exposure limit, as described previously, is one example of guidance provided in response to detection of an adverse condition, and associated passive content may include the display of available options to treat this condition, including the options to administer additional intravenous fluids, inotropic medications or vasopressors, or to reduce the anesthetic depth.

The dynamic guidance can include results of analysis of the data that has been obtained via the synchronization module 154 from the devices 130, encounter server 122 or other services 124 for a given patient encounter. Thus it is to be understood that the DSS server 112 can retrieve, track and provide guidance separately for each patient encounter. The guidance engine 152 thus can be programmed to present pertinent information, from both the dynamic and static content to the user based upon rules or expressions that can be configured.

The global guidance module 158 can be configured for certain groups or across an enterprise by establishing a set of global criteria upon which the guidance engine 152 will provide guidance, including passive and dynamic guidance as described herein. The global module 158, for example, can be utilized to define parameters or other criteria such as in the form of dynamic expressions that control what content displays as well as what actions are suggested to be performed. Guidance implemented within the global module 158 corresponds to guidance that is applicable to all users or a predefined set of users within the system. For instance, the global guidance module can be programmed to implement rules for providing generally applicable guidance, such as can be based upon best practices evidence or other policies and procedures for a given institution.

The personal guidance module 160 can be utilized by an individual user to control types of guidance (e.g., alerts or dynamic DSS webpage content) that is to be provided based upon user-defined parameters. In this way, each user may establish a set of personalized criteria based on which guidance can be provided to such user. Different users can employ different instances of the same personal guidance criteria (e.g., corresponding to expressions). Each instance can employ the same thresholds or different thresholds for providing associated guidance. An authorized user can also convert a personal guidance expression to a global guidance expression, such as via a corresponding user interface 162.

A user can employ the user interface 162 of the DSS server 112 that can access corresponding tools, such as may be part of a DSS manager 164. The DSS manager 164 can correspond to functions and methods that can be utilized to program or configure various aspects of the DSS 110. The accessibility of various functions and methods that can be accessed by a given user can depend upon an individual's authorization or role within the system. For example, there can be any range of roles that can be established within the system 110, which may be based upon existing authentication systems for an enterprise or network in which the system 110 is being implemented. For instance, a supervisor or other individual with a sufficient level of authorization can set the parameters for controlling the global guidance module 158.

A system administrator further may be able to create and configure interfaces, such as including one or more device interfaces 166, to control communication and retrieval of data from various resources in the system 110. Additionally, an individual user can employ the user interface 162 to access personal preferences via the DSS manager 164 such as to establish parameters that control the personal guidance module 160 for such user. The device interface 166 can be configured to provide access to the output data provided by the one or more devices 130 that may be utilized in a given active station 126. The device interface 166 thus can create a communications channel via the network for retrieving relevant data. The retrieved data can include raw data, processed data or a combination of raw and process data that can be presented in the form of content to a given user.

By way of further example, each user that is logged into the system 110 is recognized and their personal preferences and settings can be utilized for controlling what dynamic content and active guidance may be provided to the individual according to the personal guidance module 160 and other configuration settings that may be user-configurable. Both global and personal settings can be stored as DSS parameters in the DSS data 156 in the memory 116.

A notification engine 168 can be configured to establish mechanisms to be utilized for communicating information to a given user. Similar to the guidance engine 152, the notification engine 168 can employ global and personal notification methods that are applied to users that are logged into the system 110. Such global notification mechanism can include on-screen displays that can be color coded, flashing or otherwise indicate a condition that requires attention by the user-physician. The notification engine 168 can also send messages to a given user via the corresponding messaging system 150 in response to detecting certain conditions. Such conditions can be determined by the guidance engine 152, which can correspond to global guidance or personal guidance that may be set by the user.

A user can specify more than one mechanism to be utilized for sending notifications. For example, a user can configure the notification engine 168 to alert an individual of an abnormal patient condition requiring attention via text messaging, paging, email, and/or other mechanisms via which a user can receive information. Thus in response to instructions to send a notification (e.g., as determined by the guidance engine 152), the notification engine 168 can send such notification to an individual user or to a group of users according to the notification parameters that have been established.

As an example, a given user that is logged into the system 110 may be an owner of a patient encounter (e.g., having responsibilities for the patient 132 (P1) in station 126). The responsible user may have a supervisor or other assistants that have also logged in and have been assigned to such station. The notification engine 168, in response to an alert being triggered via the guidance engine 152, can send the notification to each associated user via the messaging system 150. In this way, timely alerts and notifications can be made to appropriate personnel for more timely recognition of conditions such that one or more intervention can be made more quickly. As described herein, in addition to such notification, the guidance engine 152 can also generate pertinent information to guide the user in such information, such as described herein.

If the guidance engine determines the occurrence of an alert condition for a given patient 132, the corresponding alert condition can be presented to one or more users via the user device 146. A corresponding notification can also be sent to an individual user, as appropriate based on notification parameters. Once an alert condition has been presented to a user, the user can employ the user interface 148 of the user device 146 to acknowledge the condition. A user can intervene to remedy the condition, obtain additional information that may be presented to the user via the user interface 148 (e.g., guidance in the form of documents, information or policies and procedures) and take appropriate action to address the condition accordingly. Alternatively, some types of alert conditions can resolve themselves without intervention. Once the user believes that the condition has resolved itself or has taken steps to remedy the situation, a user can clear and remove the alert condition.

While the foregoing example has been described in the terms of an alert condition for an individual patient 132, the system 110 can also include a dashboard module 170 that can present information associated with a plurality of stations to one or more users, such as a supervisor of a floor or ward of operating rooms. For example, the dashboard module 170 can present information in a format (e.g., graphical information superimposed on a floor plan) that can be easily understood by a supervisor. The representation of the floor can correspond to the individual floor plan of the facility and the operating rooms therein. Tools can also be provided in the DSS server 112 to configure the floor plan to correspond to the actual floor plan in which the operating rooms or other types of stations 126 reside or can be based on certain conditions being met, such as patients being pediatric patients of less than a certain age.

Each station 126 in the representation, for example, can be color coded to provide a status indicator associated with each such station. For instance, a green color can be utilized to indicate that everything is within expected operating parameters, yellow can indicate a warning condition, such as a previous alert condition that has resolved, and red can be utilized to indicate an active alert condition. Additionally, icons or other information can be presented in a graphical user interface element for each station 126. For instance, the icons can be utilized to present a user with an indication of the patient condition such as real-time vital signs or other relevant patient information. The individual station user interface elements can also be populated with information including the severity and duration of physiological aberration (e.g., hypotension) in response to the guidance engine 152 determining a corresponding alert condition exists.

Furthermore, locations may be highlighted by different methods of emphasis such as boldness or color of the outline and frame in case of any conditions that may require special attention, such as new conditions (i.e., conditions that did not exist in the immediately preceding time period) and conditions that persist beyond a certain time limit deemed to correspond to a certain level of risk, or conditions that may indicate progressive risk such as that attributable to an increasing number of hypotensive exposure limits that were exceeded Any number of one or more criteria can be established for providing decision support guidance that can be presented via the dashboard for each of the plurality of stations. If an alert condition exists, a corresponding icon associated with such condition can be represented in the station graphical user interface element to indicate a particular condition. By hovering a cursor over a given icon, additional information about the alert condition can be provided to the user. The user can take appropriate action based on the information presented via the dashboard, such as may include contacting an individual who is assigned to such station (the supervising physician) Additionally, the alert can provide impetus for monitoring a given station to ensure that appropriate action is taken to resolve the condition in a timely manner. For example, after a condition has been resolved for a given station 126, the guidance engine 152 can change the condition from an alert condition to a warning condition such that the station user interface element can change from red (the alert condition) to a yellow color (a warning color) to indicate that the condition has resolved. When a condition has been resolved, but has not been cleared (corresponding to a warning condition—yellow), an individual can hover a cursor over the user interface element or icon exhibiting the warning condition and be presented information about the previous alert condition or conditions. For example, if a patient has hypertension and the hypertension resolves itself, by hovering over the icon for the corresponding station, a given user can be informed of the extent of the hypertension, the time period that the hypertension occurred and when it was resolved. Additional information about its resolution as well as other vitals can also be provided, if so configured. The user can be given an option to clear the warning condition or take other action, understanding that a person may be prone to a given condition.

Furthermore, the color coding can be configured in such a way that resolving physiologic aberrations can be reflected in a gradual color change back to normal over a period of time that is either pre-configurable or related to the rate of improvement of the physiologic state.

In addition to information about patient health, the guidance engine 152 can also provide information relating to equipment and the devices 130 in each station such as in response to detecting a potential malfunction of such devices or the user of such devices. As an example, the guidance engine 152 can be programmed (e.g., via a corresponding expression) to detect a situation when a patient's blood pressure has not been taken within a predetermined time period (such as within the preceding 5 minutes). If the blood pressure reading has not been taken within such predetermined period, based on the expression, an alert can be triggered and a notification engine 168 can distribute such notification based upon the notification parameters. Concurrently with such notification and determination that blood pressure has not been taken the search module 172 can selectively query one or more databases such as forming part of the system data 120, to obtain information relevant to the failure of the blood pressure to be taken, to provide additional assistance to the user relevant to the current alert condition, such as potential causes including that of the blood pressure monitoring device being switched off. The search module 172 further can be customized for a given user, via the user interface 162 such as to implement custom search strings for obtaining relevant data for a given station 126. Corresponding queries thus can be created in response to the guidance engine 152 detecting the occurrence of a given condition to which the search string has been associated.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

Having described the invention, the following is claimed:

1. A method for monitoring a patient under anesthesia during a procedure comprising:

monitoring an arterial blood pressure of a patient during a procedure at an associated sensor;

measuring respective cumulative times for which the monitored arterial blood pressure of the patient falls below each of a plurality of threshold values during the procedure;

calculating a risk metric for the patient, representing an effect of arterial blood pressure on a patient outcome related to the procedure from the measured cumulative times for which the arterial blood pressure of the patient met each of the plurality of threshold values, as a linear combination of respective step functions of the measured cumulative times, such that the linear combination of the respective step functions of the cumulative times comprises a number of cumulative times that exceed a value associated with their associated step function;

calculating a risk index, representing a chance in a probability of the patient outcome related to the procedure, as an exponential function of the risk metric; and adjusting a level of anesthesia provided to the patient according to the calculated risk metric, such that further increase in the risk metric is minimized.

2. The method of claim 1, further comprising alerting an operator each time a cumulative time exceeds the value associated with its associated step function.

3. The method of claim 1, wherein the values associated with the step functions for the plurality of cumulative times are determined according to at least one biometric parameter of the patient.

4. The method of claim 3, wherein the arterial blood pressure is a mean arterial blood pressure and the plurality of threshold values comprise mean arterial blood pressure values equivalent to each integer value between forty-five mmHg and seventy-five mmHg.

5. The method of claim 1, further comprising alerting an operator each time the calculated risk metric changes.

6. A non-transitory computer readable medium storing machine executable instructions executable at an associated processor to predict patient outcomes related to a procedure, the instructions comprising:

a feature extractor configured to monitor a physiological parameter for a patient during the procedure and determine, for each of a plurality of threshold values for the metric, a cumulative time period for which the monitored physiological parameter meets the threshold value;

a predictive model configured to calculate a risk metric as a number of the plurality of threshold, values for which the determined cumulative time is greater than a maximum time associated with the threshold value, and calculate a risk index as an exponential function of the risk metric; and a user interface configured to provide one of the calculated risk metric and the calculated risk index to a user in a human comprehensible form.

7. The non-transitory computer readable medium of claim 6, the instructions further being configured to receive a plurality of parameters derived from physiological measurements taken during the procedure from associated sensors.

8. The non-transitory computer readable medium of claim 6, wherein the user interface is configured to alert an operator whenever a measured cumulative time exceeds a predetermined value for its associated threshold value.

9. The non-transitory computer readable medium of claim 8, wherein the user interface monitors a plurality of patients at a remote location and alerts the operator whenever a measured cumulative time exceeds a predetermined value for its associated threshold value for any of the plurality of patients.

10. The non-transitory computer readable medium of claim 6, wherein the monitored physiological parameter is a blood pressure of the patient.

11. A system, implemented on at least one dedicated hardware device, for predicting patient outcomes relating to a procedure comprising:

a sensor configured to detect a physiological parameter of a patient during the procedure;

a user interface;

a processing assembly configured to compare the detected physiological parameter to a plurality of defined ranges, record respective cumulative times for which the measured physiological parameter deviate from each of the defined ranges, notify an operator each time the cumulative time that the measured physiological parameter exceeds a maximum time associated with a given defined range, and calculate a risk index, representing a change in a probability of a patient outcome related to the procedure, as an exponential function of a number of the plurality of defined ranges for which the cumulative time for the measured physiological parameter exceeds the maximum time.

12. The system of claim 11, wherein the sensor is configured to measure a blood pressure of the patient.

13. A method for detecting hypotensive exposure during anesthesia comprising:

monitoring a blood pressure of a patient during a procedure at a blood pressure sensor;

measuring respective cumulative times for which the blood pressure of the patient was below each of a plurality of threshold values during the procedure;

calculating a risk metric for the patient, representing an effect of arterial blood pressure on a patient outcome related to the procedure from the measured cumulative times for which the arterial blood pressure of the patient met each of the plurality of threshold values, as a linear combination of respective step functions of the measured cumulative times, such that the linear combination of the respective step functions of the cumulative times comprises a number of cumulative times that exceed a value associated with their associated step function;

calculating a risk index representing a change in a probability of the patient outcome related to the procedure, as an exponential function of the risk metric; and alerting a user when the risk index increases.

14. The method of claim 13, the method further comprising assigning the patient to a course of postsurgical follow-up care according to a number of the plurality of threshold values for which the cumulative time associated with the threshold value exceeds a predetermined exposure limit.

15. The method of claim 14, wherein the blood pressure is a mean arterial blood pressure and the plurality of threshold values comprise mean arterial blood pressure values equivalent to each integer value between forty-five mmHg and seventy-five mmHg.

16. The method of claim 14 wherein the predetermined exposure limit for each of the plurality of threshold values is selected as a time period associated with a defined progressive increase in a risk of post-procedure morbidity to the patient, such that each predetermined exposure limit that is exceeded represents a same percentage increase in the odds of post-procedure morbidity to the patient.

* * * * *

UNITED STATES PATENT AND TRADEMARK OFFICE
CERTIFICATE OF CORRECTION

PATENT NO. : 9,622,709 B2
APPLICATION NO. : 14/051902
DATED : April 18, 2017
INVENTOR(S) : Wolf H. Stapelfeldt et al.

Page 1 of 1

It is certified that error appears in the above-identified patent and that said Letters Patent is hereby corrected as shown below:

Column 23, Line 16 reads "chance" should read --change--

Signed and Sealed this
Sixth Day of June, 2017

Michelle K. Lee
*Director of the United States Patent and Trademark Office*